(12) United States Patent
Bellanca et al.

(10) Patent No.: US 9,925,024 B2
(45) Date of Patent: Mar. 27, 2018

(54) DENTAL IMPLANT AND ABUTMENT TOOLS

(75) Inventors: John J. Bellanca, West Palm Beach, FL (US); Dan P. Rogers, North Palm Beach, FL (US); Stephen M. Herrington, Naples, FL (US); Ross W. Towse, Palm City, FL (US); Ralph E. Goodman, West Palm Beach, FL (US); Zachary B. Suttin, Palm Beach Gardens, FL (US); Isabel Scalise, West Palm Beach, FL (US); Michael Bobby, Boynton Beach, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 750 days.

(21) Appl. No.: 13/533,463

(22) Filed: Jun. 26, 2012

(65) Prior Publication Data

US 2013/0004916 A1    Jan. 3, 2013

Related U.S. Application Data

(60) Provisional application No. 61/502,091, filed on Jun. 28, 2011.

(51) Int. Cl.
*A61C 8/00* (2006.01)

(52) U.S. Cl.
CPC ............ *A61C 8/0089* (2013.01); *A61C 8/006* (2013.01); *A61C 8/0018* (2013.01);
(Continued)

(58) Field of Classification Search
CPC ... A61C 8/0089; A61C 8/0057; A61C 8/0066; A61C 8/006; A61C 8/0068; A61C 8/0018; A61C 8/0059; A61C 8/0022
(Continued)

(56) References Cited

U.S. PATENT DOCUMENTS

| 711,324 A | 10/1902 | Lacy .............................. 433/173 |
| 2,276,470 A | 3/1942 | Dodelin .......................... 81/451 |

(Continued)

FOREIGN PATENT DOCUMENTS

| CA | 2230615 | 8/1997 | ............... A61C 8/00 |
| DE | 3300764 | 7/1984 | ............... A61C 8/00 |

(Continued)

OTHER PUBLICATIONS

Ospol. Abutment Remover. [online], [retrieved on Sep. 26, 2012]. Retrieved from the Internet URL: <http://www.ospol.com/?id=1304>.

(Continued)

*Primary Examiner* — Matthew Nelson
(74) *Attorney, Agent, or Firm* — Schwegman Lundberg & Woessner, P.A.

(57) ABSTRACT

A dental restoration system is disclosed including an implant for attachment to a jaw bone of a patient. The implant includes a cylindrical body having an interior bore formed between a distal end and a proximal end. An abutment includes an interior bore formed through the stem and the post and an interface section interfacing with the abutment interface of the dental implant. An abutment removal insert has a cylindrical end insertable into a groove formed in the interior bore of the abutment. An abutment removal tool screw is insertable within the abutment removal insert. The abutment removal tool screw includes a grip and an opposite end. The opposite end causes the abutment removal insert to contact the abutment. The grip is rotatable to cause the opposite end to create force against the implant to cause the abutment to be detached from the implant.

10 Claims, 11 Drawing Sheets

(52) U.S. Cl.
CPC .......... *A61C 8/0057* (2013.01); *A61C 8/0059* (2013.01); *A61C 8/0066* (2013.01); *A61C 8/0068* (2013.01); *A61C 8/0022* (2013.01)

(58) Field of Classification Search
USPC .................. 433/141, 147, 165, 172–176
See application file for complete search history.

(56) References Cited

U.S. PATENT DOCUMENTS

| | | | |
|---|---|---|---|
| 3,514,858 A | 6/1970 | Silverman | 32/2 |
| 3,618,212 A | 11/1971 | Weissman | 32/10 A |
| 3,643,658 A | 2/1972 | Steinemenan | 128/92 D |
| 3,726,011 A | 4/1973 | Savignano | 32/10 A |
| 3,760,502 A | 9/1973 | Hirsch | 32/8 |
| 3,777,346 A | 12/1973 | Steinemann | 29/180 |
| 3,919,723 A | 11/1975 | Heimke et al. | 3/1.9 |
| 3,971,135 A | 7/1976 | Leu | 32/48 |
| 4,011,602 A | 3/1977 | Rybicki et al. | 3/1.9 |
| 4,040,129 A | 8/1977 | Steinemann et al. | 3/1.9 |
| 4,072,070 A | 2/1978 | Finn | 81/71 |
| 4,158,256 A | 6/1979 | Wiland et al. | 32/12 |
| 4,179,810 A | 12/1979 | Kirsch | 433/75 |
| 4,180,910 A | 1/1980 | Straumann et al. | 433/173 |
| 4,185,383 A | 1/1980 | Heimke et al. | 433/173 |
| 4,219,015 A | 8/1980 | Steinemann | 128/92 D |
| 4,234,309 A | 11/1980 | Sellers | 433/225 |
| 4,293,302 A | 10/1981 | Hassler et al. | 433/173 |
| 4,324,549 A | 4/1982 | Madray | 433/169 |
| 4,328,593 A | 5/1982 | Sutter et al. | 3/1.91 |
| 4,332,036 A | 6/1982 | Sutter et al. | 3/1.91 |
| 4,380,436 A | 4/1983 | Kipp | 433/182 |
| 4,388,921 A | 6/1983 | Sutter et al. | 128/92 B |
| 4,416,629 A | 11/1983 | Mozsary et al. | 433/174 |
| 4,424,037 A | 1/1984 | Ogino et al. | 433/173 |
| 4,444,310 A | 4/1984 | Odell | 206/366 |
| 4,447,209 A | 5/1984 | Sutter | 433/173 |
| 4,484,570 A | 11/1984 | Sutter et al. | 128/92 D |
| 4,486,178 A | 12/1984 | Schulte | 433/173 |
| 4,490,116 A | 12/1984 | Deutsch et al. | 433/215 |
| 4,540,367 A | 9/1985 | Sulc | 433/181 |
| 4,560,353 A | 12/1985 | Schulte et al. | 433/173 |
| 4,571,185 A | 2/1986 | Rota | 433/173 |
| 4,591,483 A | 5/1986 | Nawaz | 420/463 |
| 4,600,388 A | 7/1986 | Linkow | 433/176 |
| 4,626,214 A | 12/1986 | Artal | 433/174 |
| 4,657,510 A | 4/1987 | Gittleman | 433/173 |
| 4,671,410 A | 6/1987 | Hansson et al. | 206/438 |
| 4,671,768 A | 6/1987 | Ton | 433/174 |
| 4,681,542 A | 7/1987 | Baum | 433/172 |
| 4,687,443 A | 8/1987 | Driskell | 433/173 |
| 4,710,075 A | 12/1987 | Davison | 408/202 |
| 4,712,681 A | 12/1987 | Branemark et al. | 206/438 |
| 4,714,076 A | 12/1987 | Comte et al. | 128/92 |
| 4,715,817 A | 12/1987 | Zuest et al. | 433/181 |
| 4,722,688 A | 2/1988 | Lonca | 433/173 |
| 4,722,733 A | 2/1988 | Howson | 604/411 |
| 4,731,085 A | 3/1988 | Koch | 623/16 |
| 4,744,754 A | 5/1988 | Ross | 433/173 |
| 4,756,691 A | 7/1988 | Pilarek | 433/177 |
| 4,758,161 A | 7/1988 | Niznick | 433/173 |
| 4,759,768 A | 7/1988 | Hermann et al. | 623/21 |
| 4,763,788 A | 8/1988 | Jorneus et al. | 206/438 |
| 4,772,204 A | 9/1988 | Söderberg | 433/174 |
| 4,793,808 A | 12/1988 | Kirsch | 433/173 |
| 4,803,976 A | 2/1989 | Frigg et al. | 128/92 |
| 4,824,372 A | 4/1989 | Jorneus et al. | 433/173 |
| 4,826,434 A | 5/1989 | Krueger | 433/174 |
| 4,846,683 A | 7/1989 | Lazzara et al. | 433/173 |
| 4,850,870 A | 7/1989 | Lazzara et al. | 433/174 |
| 4,850,873 A | 7/1989 | Lazzara et al. | 433/220 |
| 4,854,872 A | 8/1989 | Detsch | 433/173 |
| 4,856,648 A | 8/1989 | Krueger | 206/63.5 |
| 4,856,994 A | 8/1989 | Lazzara et al. | 433/173 |
| 4,865,648 A | 9/1989 | Kito et al. | 106/21 |
| 4,872,839 A | 10/1989 | Brajnovic | 433/173 |
| 4,875,475 A | 10/1989 | Comte et al. | 128/924 |
| 4,880,006 A | 11/1989 | Albrektsson et al. | 128/630 |
| 4,881,897 A | 11/1989 | Franek et al. | 433/169 |
| 4,906,191 A | 3/1990 | Soderberg | 433/213 |
| 4,906,420 A | 3/1990 | Brajnovic et al. | 264/17 |
| 4,917,703 A | 4/1990 | Albrektsson | 623/66 |
| 4,936,313 A | 6/1990 | Burkhardt et al. | 128/751 |
| 4,955,811 A | 9/1990 | Lazzara et al. | 433/173 |
| 4,960,381 A | 10/1990 | Niznick | 433/174 |
| 4,978,007 A | 12/1990 | Jacobs et al. | 206/469 |
| 4,983,184 A | 1/1991 | Steinemann | 623/66 |
| 4,988,298 A | 1/1991 | Lazzara et al. | 433/173 |
| 4,995,810 A | 2/1991 | Soderberg | 433/141 |
| 5,000,685 A | 3/1991 | Brajnovic | 433/173 |
| 5,002,542 A | 3/1991 | Frigg | 606/61 |
| 5,006,069 A | 4/1991 | Lazzara et al. | 433/173 |
| 5,006,070 A | 4/1991 | Komatsu | 433/176 |
| 5,015,186 A | 5/1991 | Detsch | 433/173 |
| 5,019,083 A | 5/1991 | Klapper et al. | 606/99 |
| 5,022,860 A | 6/1991 | Lazzara et al. | 433/174 |
| 5,026,285 A | 6/1991 | Dürr et al. | 433/173 |
| 5,030,094 A | 7/1991 | Nardi et al. | 433/169 |
| 5,030,096 A | 7/1991 | Hurson et al. | 433/173 |
| 5,035,619 A | 7/1991 | Daftary | 433/173 |
| 5,040,983 A | 8/1991 | Binon | 433/173 |
| 5,045,054 A | 9/1991 | Hood et al. | 604/22 |
| 5,049,072 A | 9/1991 | Lueschen | 433/173 |
| 5,049,073 A | 9/1991 | Lauks | 433/173 |
| 5,049,074 A | 9/1991 | Otani et al. | 433/173 |
| 5,052,930 A | 10/1991 | Lodde et al. | 433/173 |
| 5,052,931 A | 10/1991 | Kirsch | 433/173 |
| 5,061,181 A | 10/1991 | Niznick | 433/174 |
| 5,061,285 A | 10/1991 | Koch | 623/16 |
| 5,062,800 A | 11/1991 | Niznick | 433/229 |
| 5,064,375 A | 11/1991 | Jorneus | 433/229 |
| 5,069,622 A | 12/1991 | Rangert et al. | 433/173 |
| 5,071,350 A | 12/1991 | Niznick | 433/173 |
| 5,071,351 A | 12/1991 | Green, Jr. et al. | 433/173 |
| 5,073,111 A | 12/1991 | Daftary | 433/173 |
| 5,076,788 A | 12/1991 | Niznick | 433/173 |
| RE33,796 E | 1/1992 | Niznick | 433/173 |
| 5,078,605 A | 1/1992 | Sutter et al. | 433/165 |
| 5,080,685 A | 1/1992 | Bolesky et al. | 623/23 |
| 5,100,323 A | 3/1992 | Friedman et al. | 433/173 |
| 5,105,690 A | 4/1992 | Lazzara et al. | 81/436 |
| 5,106,300 A | 4/1992 | Voitik | 433/173 |
| 5,116,225 A | 5/1992 | Riera | 433/173 |
| 5,120,221 A | 6/1992 | Orenstein et al. | 433/159 |
| 5,120,222 A | 6/1992 | Sulc | 433/181 |
| 5,122,059 A | 6/1992 | Dürr et al. | 433/173 |
| 5,125,840 A | 6/1992 | Dürr et al. | 433/173 |
| 5,125,841 A | 6/1992 | Carlsson et al. | 433/213 |
| 5,135,395 A | 8/1992 | Marlin | 433/174 |
| 5,140,877 A | 8/1992 | Sloan | 81/439 |
| 5,145,371 A | 9/1992 | Jörnéus | 433/173 |
| 5,145,372 A | 9/1992 | Daftary et al. | 433/173 |
| 5,154,612 A | 10/1992 | Carlsson et al. | 433/173 |
| 5,158,458 A | 10/1992 | Perry | 433/141 |
| 5,174,755 A | 12/1992 | Fukuda | 433/173 |
| 5,180,303 A | 1/1993 | Hornburg et al. | 433/173 |
| 5,181,928 A | 1/1993 | Bolesky et al. | 623/23 |
| 5,188,800 A | 2/1993 | Green, Jr. et al. | 422/23 |
| 5,190,543 A | 3/1993 | Schläpfer | 606/61 |
| 5,195,891 A | 3/1993 | Sulc | 433/173 |
| 5,195,892 A | 3/1993 | Gersberg | 433/174 |
| 5,196,016 A | 3/1993 | Buser et al. | 606/72 |
| 5,197,881 A | 3/1993 | Chalifoux | 433/173 |
| 5,199,873 A | 4/1993 | Schulte et al. | 433/174 |
| 5,209,659 A | 5/1993 | Friedman et al. | 433/173 |
| 5,209,666 A | 5/1993 | Balfour et al. | 433/173 |
| 5,211,561 A | 5/1993 | Graub | 433/169 |
| 5,213,500 A | 5/1993 | Salazar et al. | 433/169 |
| 5,213,502 A | 5/1993 | Daftary | 433/172 |
| 5,215,460 A | 6/1993 | Perry | 433/75 |
| 5,238,405 A | 8/1993 | Marlin | 433/173 |
| D339,419 S | 9/1993 | Hood et al. | D24/146 |
| 5,246,368 A | 9/1993 | Sillard | 433/167 |
| 5,246,370 A | 9/1993 | Coatoam | 433/173 |
| D340,981 S | 11/1993 | Hood et al. | D24/146 |

(56) References Cited

U.S. PATENT DOCUMENTS

| | | | |
|---|---|---|---|
| D341,201 S | 11/1993 | Hood et al. | D24/146 |
| D341,202 S | 11/1993 | Hood et al. | D24/146 |
| D342,313 S | 12/1993 | Hood et al. | D24/146 |
| 5,281,140 A | 1/1994 | Niznick | 433/172 |
| 5,286,195 A | 2/1994 | Clostermann | 433/172 |
| 5,292,252 A | 3/1994 | Nickerson et al. | 433/173 |
| 5,295,831 A | 3/1994 | Patterson et al. | 433/141 |
| 5,297,963 A | 3/1994 | Daftary | 433/172 |
| 5,302,125 A | 4/1994 | Kownacki et al. | 433/172 |
| 5,302,126 A | 4/1994 | Wimmer et al. | 433/173 |
| 5,306,149 A | 4/1994 | Schmid et al. | 433/173 |
| 5,312,253 A | 5/1994 | Chalifoux | 433/173 |
| 5,312,254 A | 5/1994 | Rosenlicht | 433/173 |
| 5,312,403 A | 5/1994 | Frigg | 606/54 |
| 5,316,476 A | 5/1994 | Krauser | 433/173 |
| 5,318,570 A | 6/1994 | Hood et al. | 606/99 |
| 5,322,443 A | 6/1994 | Beaty | 433/141 |
| 5,324,297 A | 6/1994 | Hood et al. | 606/99 |
| 5,328,371 A | 7/1994 | Hund et al. | 433/173 |
| 5,334,024 A | 8/1994 | Niznick | 433/173 |
| 5,336,090 A | 8/1994 | Wilson, Jr. et al. | 433/172 |
| 5,338,196 A | 8/1994 | Beaty et al. | 433/172 |
| 5,344,457 A | 9/1994 | Pilliar et al. | 623/16 |
| 5,362,234 A | 11/1994 | Salazar et al. | 433/169 |
| 5,362,237 A | 11/1994 | Chalifoux | 433/220 |
| 5,368,160 A | 11/1994 | Leuschen et al. | 206/339 |
| 5,368,443 A | 11/1994 | Turkia et al. | 416/184 |
| 5,368,480 A | 11/1994 | Balfour et al. | 433/141 |
| 5,368,483 A | 11/1994 | Sutter et al. | 433/173 |
| 5,376,004 A | 12/1994 | Mena | 433/173 |
| 5,387,102 A | 2/1995 | Wagner et al. | 433/173 |
| 5,399,090 A | 3/1995 | Padros-Fradera | 433/173 |
| 5,403,136 A | 4/1995 | Mathys | 411/310 |
| 5,417,570 A | 5/1995 | Zuest et al. | 433/177 |
| 5,419,702 A | 5/1995 | Beaty et al. | 433/214 |
| 5,431,567 A | 7/1995 | Daftary | 433/172 |
| 5,433,607 A | 7/1995 | Schmid et al. | 433/173 |
| 5,433,665 A | 7/1995 | Beaty et al. | 464/38 |
| 5,437,550 A | 8/1995 | Beaty et al. | 433/141 |
| 5,437,551 A | 8/1995 | Chalifoux | 433/173 |
| 5,447,434 A | 9/1995 | Shaw | 433/173 |
| 5,449,291 A | 9/1995 | Lueschen et al. | 433/173 |
| 5,452,219 A | 9/1995 | Dehoff et al. | 364/474.05 |
| 5,456,723 A | 10/1995 | Steinemann et al. | 623/16 |
| 5,462,436 A | 10/1995 | Beaty | 433/141 |
| 5,468,150 A | 11/1995 | Brammann | 433/173 |
| 5,476,383 A | 12/1995 | Beaty et al. | 433/214 |
| 5,489,210 A | 2/1996 | Hanosh | 433/173 |
| 5,492,471 A | 2/1996 | Singer | 433/172 |
| 5,502,087 A | 3/1996 | Tateosian et al. | 523/115 |
| 5,520,689 A | 5/1996 | Schlapfer et al. | 606/61 |
| 5,527,182 A | 6/1996 | Wolloughby | 433/172 |
| 5,538,426 A | 7/1996 | Harding et al. | 433/172 |
| 5,538,428 A | 7/1996 | Staubli | 433/173 |
| 5,547,377 A | 8/1996 | Daftary | 433/172 |
| 5,554,028 A | 9/1996 | Hare et al. | 433/214 |
| 5,556,280 A | 9/1996 | Pelak | 433/172 |
| 5,562,448 A | 10/1996 | Mushabac | 433/215 |
| 5,562,733 A | 10/1996 | Weissbach et al. | 623/16 |
| 5,564,921 A | 10/1996 | Marlin | 433/172 |
| 5,564,924 A | 10/1996 | Kwan | 433/173 |
| 5,567,155 A | 10/1996 | Hansen | 433/172 |
| 5,569,035 A | 10/1996 | Balfour et al. | 433/165 |
| 5,582,299 A | 10/1996 | Lazzara et al. | 206/63.5 |
| 5,571,188 A | 11/1996 | Ellingsen et al. | 623/16 |
| 5,588,838 A | 12/1996 | Hansson et al. | 433/173 |
| 5,591,029 A | 1/1997 | Zuest | 433/173 |
| 5,605,457 A | 2/1997 | Bailey et al. | 433/173 |
| 5,607,304 A | 3/1997 | Bailey et al. | 433/174 |
| 5,626,227 A | 5/1997 | Wagner et al. | 206/369 |
| 5,628,630 A | 5/1997 | Misch et al. | 433/174 |
| 5,630,717 A | 5/1997 | Zuest et al. | 433/172 |
| 5,636,989 A | 6/1997 | Somborac et al. | 433/173 |
| 5,651,675 A | 7/1997 | Singer | 433/172 |
| 5,658,147 A | 8/1997 | Phimmasone | 433/213 |
| 5,660,545 A | 8/1997 | Bailey et al. | 433/173 |
| 5,662,476 A | 9/1997 | Inger et al. | 433/213 |
| 5,667,384 A | 9/1997 | Sutter et al. | 433/172 |
| 5,674,069 A | 10/1997 | Osorio | 433/172 |
| 5,674,071 A | 10/1997 | Beaty et al. | 433/172 |
| 5,674,072 A | 10/1997 | Moser et al. | 433/173 |
| 5,674,073 A | 10/1997 | Ingber et al. | 433/213 |
| 5,674,244 A | 10/1997 | Mathys | 606/208 |
| 5,678,995 A | 10/1997 | Kirsch et al. | 433/169 |
| 5,681,167 A | 10/1997 | Lazarof | 433/174 |
| 5,685,715 A | 11/1997 | Beaty et al. | 433/173 |
| 5,688,123 A | 11/1997 | Meiers et al. | 433/173 |
| 5,692,904 A | 12/1997 | Beaty et al. | 433/141 |
| 5,695,335 A | 12/1997 | Haas et al. | 433/173 |
| 5,704,788 A | 1/1998 | Milne | 433/173 |
| 5,725,377 A | 3/1998 | Lemler et al. | 433/173 |
| 5,730,598 A | 3/1998 | Story et al. | 433/201.1 |
| 5,733,122 A | 3/1998 | Gordon | 433/172 |
| 5,733,123 A | 3/1998 | Blacklock et al. | 433/173 |
| 5,734,113 A | 3/1998 | Vogt et al. | 73/862.23 |
| 5,741,253 A | 4/1998 | Michelson | 606/61 |
| 5,749,731 A | 5/1998 | Morgan et al. | 433/173 |
| 5,752,830 A | 5/1998 | Suarez | 433/173 |
| 5,752,831 A | 5/1998 | Padros-Fradera | 433/173 |
| 5,755,574 A | 5/1998 | D'Alise | 433/173 |
| 5,755,807 A | 5/1998 | Anstaett et al. | 623/23 |
| 5,759,033 A | 6/1998 | Elia | 433/173 |
| 5,759,034 A | 6/1998 | Daftary | 433/173 |
| 5,759,036 A | 6/1998 | Hinds | 433/214 |
| 5,762,500 A | 6/1998 | Lazarof | 433/213 |
| 5,762,541 A | 6/1998 | Heath et al. | 451/48 |
| 5,766,009 A | 6/1998 | Jeffcoat | 433/173 |
| 5,779,480 A | 7/1998 | Groll et al. | 433/173 |
| 5,782,637 A | 7/1998 | Cosenza | 433/173 |
| 5,782,918 A | 7/1998 | Klardie et al. | 623/16 |
| 5,785,525 A | 7/1998 | Weissman | 433/174 |
| 5,810,589 A | 9/1998 | Michnick et al. | 433/169 |
| 5,810,590 A | 9/1998 | Fried et al. | 433/172 |
| 5,816,812 A | 10/1998 | Kownacki et al. | 433/174 |
| 5,820,374 A | 10/1998 | Simmons et al. | 433/173 |
| 5,823,776 A | 10/1998 | Duerr et al. | 433/173 |
| 5,823,777 A | 10/1998 | Misch et al. | 433/174 |
| 5,827,062 A | 10/1998 | Driskell et al. | 433/173 |
| D401,695 S | 11/1998 | Daftary | D24/155 |
| 5,829,977 A | 11/1998 | Rogers et al. | 433/172 |
| 5,829,981 A | 11/1998 | Ziegler | 433/214 |
| 5,836,768 A | 11/1998 | Hüskens et al. | 433/173 |
| 5,842,865 A | 12/1998 | Bassett et al. | 433/174 |
| 5,858,253 A | 1/1999 | Holm | 210/702 |
| D405,179 S | 2/1999 | Kirsch et al. | D24/154 |
| 5,865,622 A | 2/1999 | Aleksey | 433/177 |
| 5,871,358 A | 2/1999 | Ingber et al. | 433/213 |
| 5,871,504 A | 2/1999 | Eaton et al. | 606/232 |
| 5,882,200 A | 3/1999 | Sutter et al. | 433/173 |
| 5,888,218 A | 3/1999 | Folsom | 623/16 |
| 5,897,320 A | 4/1999 | Gittleman | 433/180 |
| D410,083 S | 5/1999 | Broberg et al. | D24/156 |
| 5,899,940 A | 5/1999 | Carchidi et al. | 623/16 |
| 5,904,483 A | 5/1999 | Wade | 433/173 |
| 5,906,488 A | 5/1999 | Kvarnström | 433/116 |
| 5,915,968 A | 6/1999 | Kirsch et al. | 433/173 |
| 5,927,979 A | 7/1999 | Misch et al. | 433/173 |
| 5,931,674 A | 8/1999 | Hanosh et al. | 433/173 |
| 5,938,443 A | 8/1999 | Lazzara et al. | 433/173 |
| 5,938,444 A | 8/1999 | Hansson et al. | 433/174 |
| 5,938,446 A | 8/1999 | Andersson et al. | 433/223 |
| 5,944,526 A | 8/1999 | Liu | 433/176 |
| D414,556 S | 9/1999 | Broberg et al. | D24/156 |
| 5,947,733 A | 9/1999 | Sutter et al. | 433/173 |
| 5,947,734 A | 9/1999 | Hanel | 433/173 |
| 5,947,736 A | 9/1999 | Behrend | 433/214 |
| 5,951,287 A | 9/1999 | Hawkinson | 433/173 |
| 5,951,288 A | 9/1999 | Sawa | 433/173 |
| 5,952,399 A | 9/1999 | Rentsch | 523/116 |
| 5,954,504 A | 9/1999 | Misch et al. | 433/174 |
| 5,954,505 A | 9/1999 | Ford | 433/177 |
| 5,961,328 A | 10/1999 | Somborac et al. | 433/173 |
| 5,961,329 A | 10/1999 | Stucki-McCormick | 433/173 |
| 5,964,591 A | 10/1999 | Beaty et al. | 433/173 |

(56) References Cited

U.S. PATENT DOCUMENTS

| | | | |
|---|---|---|---|
| 5,975,902 A | 11/1999 | Emmanuel | 433/173 |
| 5,979,643 A | 11/1999 | Blonder et al. | 206/63.5 |
| 5,984,680 A | 11/1999 | Rogers | 433/173 |
| 5,989,028 A | 11/1999 | Niznick | 433/173 |
| 5,989,029 A | 11/1999 | Osorio et al. | 433/173 |
| 5,993,211 A | 11/1999 | Broberg | 433/172 |
| 5,993,214 A | 11/1999 | Persson | 433/223 |
| 6,007,337 A | 12/1999 | Bauer | 433/173 |
| 6,012,923 A | 1/2000 | Bassett et al. | 433/172 |
| 6,030,219 A | 2/2000 | Zuest et al. | 433/181 |
| 6,033,218 A | 3/2000 | Bergström et al. | 433/72 |
| 6,036,491 A | 3/2000 | Hansson | 433/174 |
| 6,039,568 A | 3/2000 | Hinds | 433/175 |
| 6,045,361 A | 4/2000 | Misch et al. | 433/214 |
| 6,048,204 A | 4/2000 | Klardie et al. | 433/174 |
| 6,053,733 A | 4/2000 | Aspichueta et al. | 433/173 |
| 6,053,920 A | 4/2000 | Carlsson et al. | 606/72 |
| 6,066,274 A | 5/2000 | Antonson et al. | 264/16 |
| 6,068,478 A | 5/2000 | Grande et al. | 433/172 |
| 6,068,479 A | 5/2000 | Kwan | 433/173 |
| 6,068,480 A * | 5/2000 | Misch | A61C 8/0001 433/173 |
| 6,076,660 A | 6/2000 | Day | 206/63.5 |
| 6,083,004 A | 7/2000 | Misch et al. | 433/173 |
| 6,086,371 A | 7/2000 | Bassett et al. | 433/173 |
| 6,093,023 A | 7/2000 | Sala Meseguer | 433/173 |
| 6,099,311 A | 8/2000 | Wagner et al. | 433/173 |
| 6,102,702 A | 8/2000 | Folsom, Jr. et al. | 433/172 |
| 6,116,904 A | 9/2000 | Kirsch et al. | 433/173 |
| 6,120,292 A | 9/2000 | Buser et al. | 433/173 |
| 6,142,782 A | 11/2000 | Lazarof | 433/174 |
| 6,146,387 A | 11/2000 | Trott et al. | 606/104 |
| 6,149,432 A | 11/2000 | Shaw et al. | 433/174 |
| 6,149,433 A | 11/2000 | Ziegler et al. | 433/214 |
| 6,155,828 A | 12/2000 | Lazzara et al. | 433/173 |
| 6,159,008 A | 12/2000 | Kumar | 433/163 |
| 6,159,244 A | 12/2000 | Suddaby | 623/17.11 |
| 6,168,436 B1 | 1/2001 | O'Brien | 433/173 |
| 6,193,516 B1 | 2/2001 | Story | 433/173 |
| 6,196,842 B1 | 3/2001 | Jörnéus | 433/174 |
| 6,203,323 B1 | 3/2001 | Beaty et al. | 433/173 |
| 6,206,696 B1 * | 3/2001 | Day | A61C 8/008 433/141 |
| 6,208,813 B1 | 3/2001 | Carlsson et al. | 396/324 |
| 6,213,773 B1 | 4/2001 | Gittleman | 433/172 |
| 6,214,007 B1 * | 4/2001 | Anderson | A61B 17/0401 606/304 |
| 6,217,331 B1 | 4/2001 | Rogers et al. | 433/173 |
| 6,217,332 B1 | 4/2001 | Kumar | 433/173 |
| 6,220,860 B1 | 4/2001 | Hansson | 433/173 |
| 6,227,858 B1 | 5/2001 | Lundgren | 433/173 |
| 6,227,859 B1 | 5/2001 | Sutter | 433/173 |
| 6,231,342 B1 | 5/2001 | Osorio et al. | 433/173 |
| 6,247,933 B1 | 6/2001 | Wagner et al. | 433/173 |
| 6,254,387 B1 | 7/2001 | Bergström et al. | 433/49 |
| 6,257,890 B1 | 7/2001 | Khoury et al. | 433/173 |
| 6,261,097 B1 | 7/2001 | Schmutz et al. | 433/173 |
| 6,261,098 B1 | 7/2001 | Persson | 433/213 |
| D446,859 S | 8/2001 | Hurson | D24/156 |
| 6,273,720 B1 | 8/2001 | Spalten | 433/173 |
| 6,273,722 B1 | 8/2001 | Phillips | 433/174 |
| 6,276,938 B1 | 8/2001 | Jörneus et al. | 433/172 |
| 6,280,195 B1 | 8/2001 | Broberg et al. | 433/201.1 |
| 6,283,752 B1 | 9/2001 | Kumar | 433/172 |
| 6,283,755 B1 | 9/2001 | Bergström et al. | 433/193 |
| 6,287,119 B1 | 9/2001 | van Nifterick et al. | 433/213 |
| 6,290,499 B1 | 9/2001 | Lazzara et al. | 433/173 |
| 6,290,500 B1 | 9/2001 | Morgan et al. | 433/173 |
| 6,305,938 B1 | 10/2001 | Brånemark | 433/173 |
| 6,305,939 B1 | 10/2001 | Dawood | 433/174 |
| 6,312,260 B1 | 11/2001 | Kumar et al. | 433/174 |
| 6,315,562 B1 | 11/2001 | Kumar | 433/173 |
| 6,315,563 B1 | 11/2001 | Sager | 433/173 |
| 6,332,777 B1 | 12/2001 | Sutter | 433/173 |
| 6,343,930 B1 | 2/2002 | Beaty et al. | 433/173 |
| 6,350,126 B1 | 2/2002 | Levisman | 433/173 |
| 6,358,050 B1 | 3/2002 | Bergström et al. | 433/173 |
| 6,358,051 B2 | 3/2002 | Lang et al. | 433/173 |
| 6,358,052 B1 | 3/2002 | Lustig et al. | 433/174 |
| 6,375,464 B1 | 4/2002 | Hollander et al. | 433/173 |
| 6,382,976 B1 | 5/2002 | Wagner | 433/174 |
| 6,394,803 B1 | 5/2002 | Salz et al. | 433/49 |
| 6,394,806 B1 | 5/2002 | Kumar | 433/173 |
| 6,394,809 B2 | 5/2002 | Rogers et al. | 433/174 |
| 6,402,515 B1 | 6/2002 | Palti et al. | 433/174 |
| 6,619,958 B2 | 9/2003 | Beaty et al. | 433/173 |
| 6,666,685 B2 | 12/2003 | Filho | 433/173 |
| 6,726,481 B1 | 4/2004 | Zickmann et al. | 433/173 |
| 6,733,291 B1 | 5/2004 | Hurson | 433/173 |
| 7,101,183 B2 | 9/2006 | Augthun et al. | 433/173 |
| 7,214,063 B2 | 5/2007 | Cohen | 433/174 |
| 7,309,231 B2 | 12/2007 | Engman | 433/173 |
| 7,338,286 B2 | 3/2008 | Porter et al. | 433/173 |
| 7,344,376 B2 | 3/2008 | Beaty et al. | 433/173 |
| 7,484,959 B2 * | 2/2009 | Porter | A61C 8/0001 433/173 |
| 7,665,990 B2 | 2/2010 | Mundwiler et al. | 433/173 |
| 8,033,826 B2 | 10/2011 | Towse et al. | 433/172 |
| 8,070,491 B2 | 12/2011 | Mundwiler et al. | 433/163 |
| 8,113,835 B2 | 2/2012 | Yau et al. | 433/173 |
| 2001/0004694 A1 * | 6/2001 | Carchidi | A61B 17/8615 606/312 |
| 2001/0037154 A1 | 11/2001 | Martin | 623/20.12 |
| 2002/0025505 A1 | 2/2002 | Beaty et al. | 433/173 |
| 2002/0106610 A1 | 8/2002 | Hurson | 433/173 |
| 2003/0224327 A1 | 12/2003 | Constantino | 433/165 |
| 2004/0038179 A1 * | 2/2004 | Kumar | A61C 8/008 433/173 |
| 2004/0101808 A1 | 5/2004 | Porter et al. | 433/173 |
| 2005/0008990 A1 * | 1/2005 | Ganz | A61C 8/0006 433/215 |
| 2005/0084820 A1 * | 4/2005 | Ashman | A61C 8/0006 433/173 |
| 2005/0113930 A1 * | 5/2005 | Ganz | A61C 8/0006 623/17.17 |
| 2005/0191600 A1 * | 9/2005 | Beaty | A61C 8/0001 433/173 |
| 2005/0214714 A1 * | 9/2005 | Wohrle | A61C 8/0018 433/173 |
| 2007/0142789 A1 * | 6/2007 | Fisher | A61M 5/3158 604/207 |
| 2008/0057477 A1 * | 3/2008 | Rosen | A61C 8/005 433/174 |
| 2008/0102420 A1 * | 5/2008 | Porter | A61C 8/0001 433/152 |
| 2008/0153062 A1 * | 6/2008 | Beaty | A61C 8/0001 433/173 |
| 2008/0182227 A1 | 7/2008 | Wolf et al. | 433/174 |
| 2008/0243123 A1 * | 10/2008 | Gordils Wallis | A61B 17/1688 606/80 |
| 2008/0261176 A1 * | 10/2008 | Hurson | A61C 8/0022 433/174 |
| 2009/0111072 A1 * | 4/2009 | Lombardo | A61C 8/005 433/174 |
| 2010/0119995 A1 | 5/2010 | Grant et al. | 433/174 |
| 2010/0248180 A1 | 9/2010 | Bondar | 433/141 |
| 2010/0266985 A1 | 10/2010 | Yau et al. | 433/173 |
| 2010/0330531 A1 | 12/2010 | Olsson et al. | |
| 2011/0008754 A1 * | 1/2011 | Bassett | A61C 8/0012 433/175 |
| 2011/0183290 A1 | 7/2011 | Galgut et al. | 433/174 |
| 2011/0250564 A1 | 10/2011 | Hung | 433/174 |
| 2012/0077151 A1 | 3/2012 | Nary Filho et al. | 433/174 |
| 2013/0004915 A1 | 1/2013 | Bellanca et al. | 433/173 |

FOREIGN PATENT DOCUMENTS

| | | | |
|---|---|---|---|
| DE | 4028855 | 3/1992 | A61C 8/00 |
| DE | 4405797 C1 | 5/1995 | |
| DE | 102009015358 A1 | 9/2010 | |
| EP | 0231730 | 8/1987 | A61C 8/00 |
| EP | 0475299 | 3/1992 | A61C 8/00 |

(56) References Cited

FOREIGN PATENT DOCUMENTS

| | | | | |
|---|---|---|---|---|
| EP | 0497082 | 8/1992 | ............... | A61C 8/00 |
| EP | 0657146 | 6/1995 | ............... | A61C 8/00 |
| EP | 0727193 | 8/1996 | ............... | A61C 8/00 |
| EP | 0735843 | 10/1996 | ............... | A61C 8/00 |
| FR | 2635455 | 2/1990 | ............... | A61C 8/00 |
| FR | 2695823 A1 | 3/1994 | | |
| JP | 11501856 A | 2/1999 | | |
| JP | 2003190188 A | 7/2003 | | |
| JP | 2004141479 A | 5/2004 | | |
| JP | 2009504248 A | 2/2009 | | |
| JP | 2010136943 A | 6/2010 | | |
| JP | 2014520599 A | 8/2014 | | |
| WO | 93/20773 | 10/1993 | ............... | A61C 8/00 |
| WO | 94/14388 | 7/1994 | ............... | A61C 8/00 |
| WO | 96/29019 | 9/1996 | ............... | A61C 8/00 |
| WO | 97/06930 | 2/1997 | ............... | A61C 8/00 |
| WO | 97/10769 | 3/1997 | ............... | A61C 8/00 |
| WO | 97/24977 | 7/1997 | ............... | A61C 8/00 |
| WO | WO-9724996 A2 | 7/1997 | | |
| WO | 97/28755 | 8/1997 | ............... | A61C 8/00 |
| WO | 98/03130 | 1/1998 | ............... | A61C 8/00 |
| WO | 98/52490 | 11/1998 | ............... | A61C 8/00 |
| WO | 98/55039 | 12/1998 | ............... | A61C 8/00 |
| WO | 99/08620 | 2/1999 | ............... | A61C 8/00 |
| WO | 00/02497 | 1/2000 | ............... | A61C 8/00 |
| WO | WO-2007021519 A2 | 2/2007 | | |
| WO | WO-2010066871 A1 | 6/2010 | | |

OTHER PUBLICATIONS

International Search Report and Written Opinion dated Sep. 24, 2012 issued in International Patent Application No. PCT/US2012/044308 (13 pages).
"U.S. Appl. No. 13/533,406, Advisory Action dated Jan. 16, 2015", 3 pgs.
"U.S. Appl. No. 13/533,406, Appeal Brief filed Mar. 30, 2015", 20 pgs.
"U.S. Appl. No. 13/533,406, Examiner's Answer dated Sep. 9, 2015", 7 pgs.
"U.S. Appl. No. 13/533,406, Final Office Action dated Jul. 17, 2013", 14 pgs.
"U.S. Appl. No. 13/533,406, Final Office Action dated Oct. 8, 2014", 17 pgs.
"U.S. Appl. No. 13/533,406, Non Final Office Action dated Jan. 3, 2014", 21 pgs.
"U.S. Appl. No. 13/533,406, Non Final Office Action dated Dec. 27, 2012", 15 pgs.
"U.S. Appl. No. 13/533,406, Reply Brief filed Nov. 5, 2015", 7 pgs.
"U.S. Appl. No. 13/533,406, Response filed Jan. 5, 2015 to Final Office Action dated Oct. 8, 2014", 9 pgs.
"U.S. Appl. No. 13/533,406, Response filed Mar. 7, 2014 to Non Final Office Action dated Jan. 3, 2014", 10 pgs.
"U.S. Appl. No. 13/533,406, Response filed Mar. 20, 2013 to Non Final Office Action dated Dec. 27, 2012", 8 pgs.
"U.S. Appl. No. 13/533,406, Response filed Nov. 15, 2013 to Final Office Action dated Jul. 17, 2013", 12 pgs.
"Application Serial No. PCT/US2012/044308, International Preliminary Report on Patentability dated Jan. 16, 2014", 12 pgs.
"European Application Serial No. 12804137.3, Extended European Search Report dated Mar. 10, 2015", 13 pgs.
"European Application Serial No. 12804137.3, Office Action dated Feb. 7, 2014", 3 pgs.
"European Application Serial No. 12804137.3, Office Action dated Mar. 27, 2015", 1 pg.
"European Application Serial No. 12804137.3, Response filed Aug. 7, 2014 to Office Action dated Feb. 7, 2014", 10 pgs.
"European Application Serial No. 12804137.3, Response filed Sep. 30, 2015 to Office Action dated Mar. 27, 2015", 13 pgs.
"European Application Serial No. 12804137.3, Supplementary European Search Report dated Nov. 17, 2014", 6 pgs.
"Japanese Application Serial No. 2014-518938, Office Action dated Mar. 22, 2016", (W/ English Translation), 10 pgs.
"Australian Application Serial No. 2012275524, First Examiner Report dated Apr. 21, 2016", 4 pgs.
"Japanese Application Serial No. 2014-518938, Response filed Sep. 14, 2016 to Office Action dated Mar. 22, 2016", W/ English Translation of Claims, 21 pgs.
"Australian Application Serial No. 2012275524, Response filed Jan. 10, 2017 to First Examiner Report dated Apr. 21, 2016", 46 pgs.
"Japanese Application Serial No. 2014-518938, Office Action dated Feb. 13, 2017", (W/ English Translation), 14 pgs.

* cited by examiner

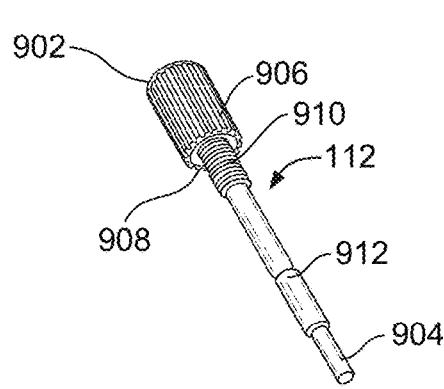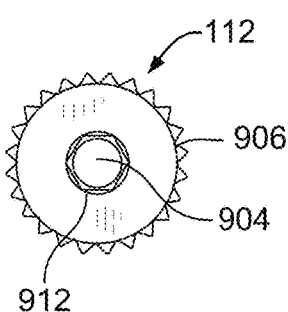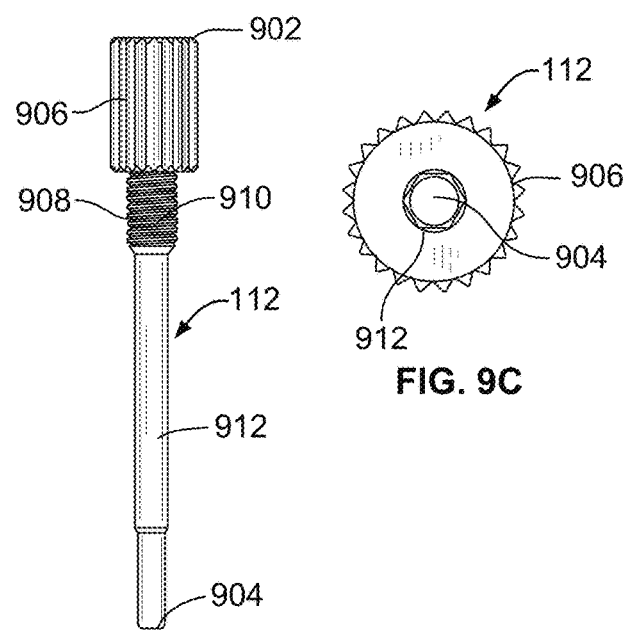
FIG. 9A
FIG. 9C
FIG. 9B
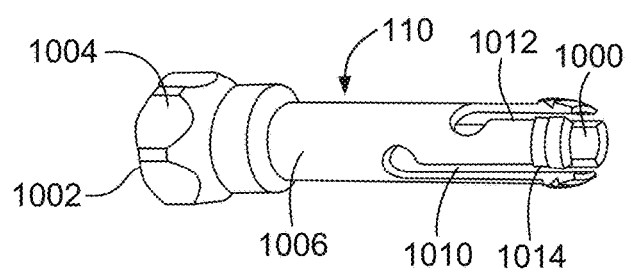
FIG. 10A
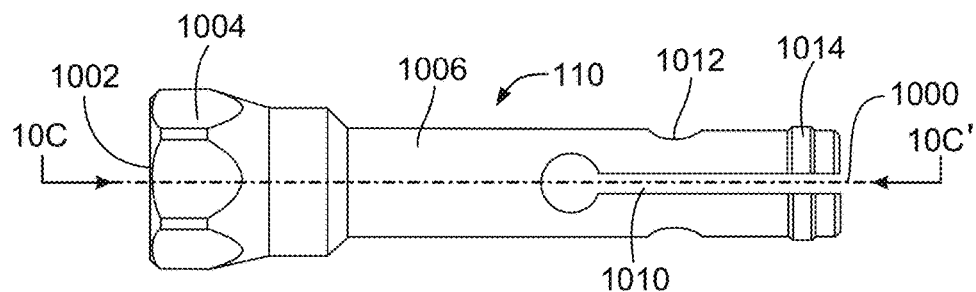
FIG. 10B

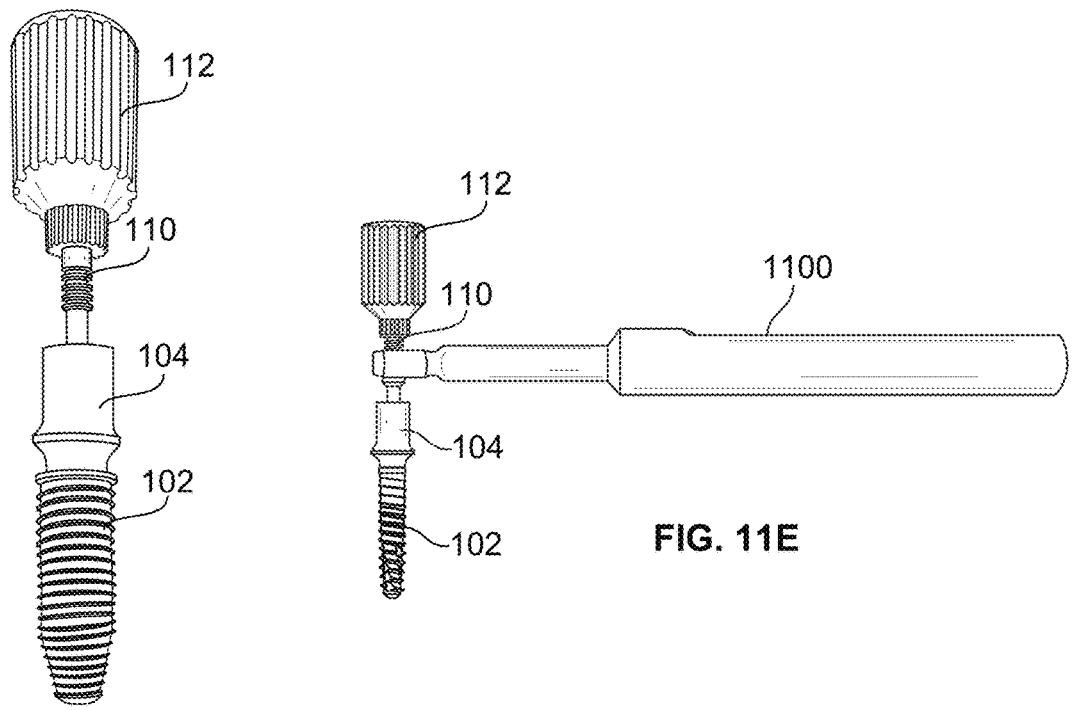
FIG. 11D
FIG. 11E
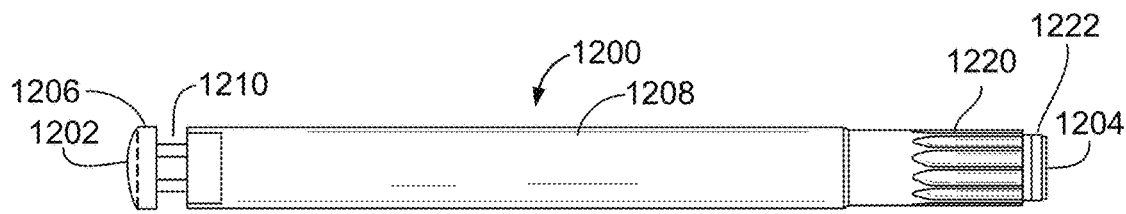
FIG. 12A
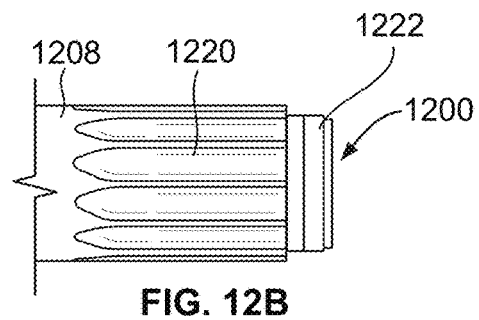
FIG. 12B

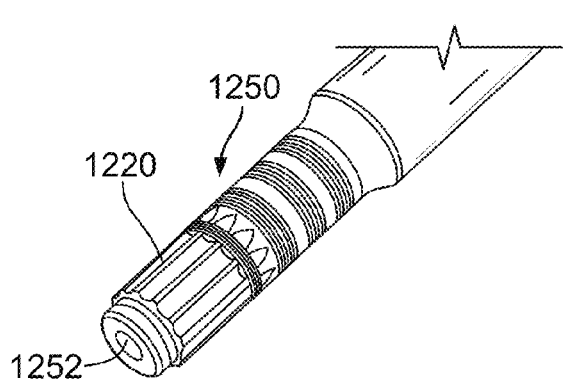
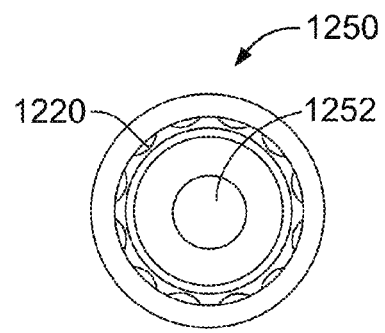
FIG.12C  FIG.12D
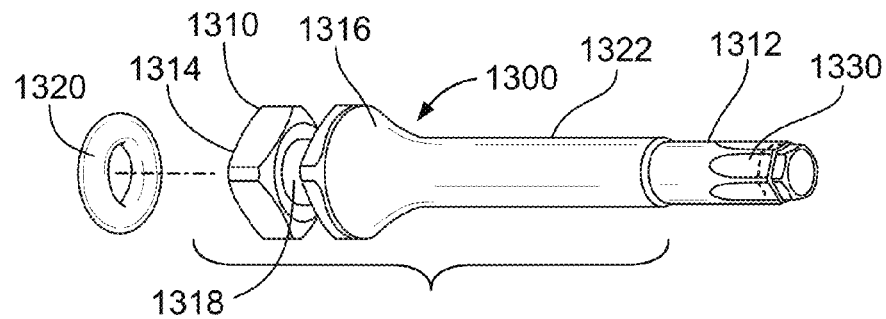
FIG. 13A
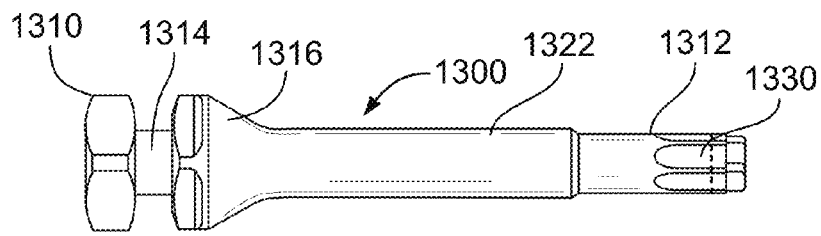
FIG. 13B
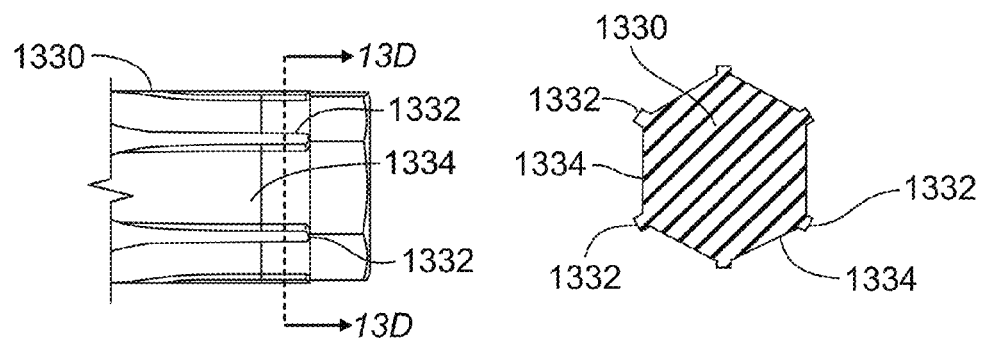
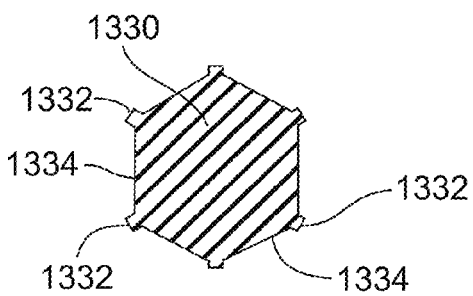
FIG. 13C  FIG. 13D

DENTAL IMPLANT AND ABUTMENT TOOLS

PRIORITY CLAIM AND CROSS REFERENCE TO RELATED APPLICATIONS

This application claims priority to U.S. Provisional Application No. 61/502,091, filed on Jun. 28, 2011 which is incorporated herein its entirety.

TECHNICAL FIELD

This disclosure relates to restorative dental implants and abutments and related tools for the assembly and disassembly of the same.

BACKGROUND

Single tooth restorations present the unique requirement that they must be supported non-rotationally on an underlying abutment. When a prepared natural tooth is the underlying abutment, this requirement is met in the normal course of preparing the abutment with a non-circular cross-section. Likewise, when the underlying abutment is a post fitted onto an implant, this requirement is met by preparing the post with a noncircular cross-section. This latter scenario can be more complicated due to the added connection between the implant and the abutment.

Typically, a dental implant is implanted into the bone of a patient's jaw and comprises a socket, e.g., a bore, which is accessible through the overlying or surrounding gum tissue for receiving and supporting one or more attachments or components which, in turn, are useful to fabricate and support the prosthodontic restoration. Dental implant procedures may use a variety of implanting modalities, for example, blade, threaded implant, or smooth push-in implant.

While numerous design iterations have been marketed, overall there have been three generations of the implant-abutment interface within these assemblies: an external hex implant, an internal connection implant, and a vertical connection assembly. The external hexagonal implant design has a hexagonal shape (or another anti-rotation feature) protruding out of the implant and the corresponding abutment has a female hexagonal receptacle. There is a surface below the hexagonal protrusion on which the abutment is seated. The hexagonal protrusion acts to constrain the abutment from rotating around the longitudinal axis as well as preventing movement on the plane coincident with the implant seating surface. Unfortunately, such an interface has virtually no stability until the screw is introduced and fully seated between the abutment and the implant. The screw is essentially the sole component resisting bending forces.

In contrast, the internal connection implant design has a hexagonal female member (or other anti-rotation feature) extruded into the implant, and the corresponding abutment has a male hexagonal protrusion. The abutment is seated on the same surface as the external hexagonal design, the only difference being that the anti-rotation feature on the implant is located below this surface. The benefit of this system is that it has intrinsic stability without the screw, and then experiences increased stability once the screw is introduced and fully seated. The system responds in a more unified manner to bending forces. While this system has advantages over the external hex implant, the disadvantage (which applies to the external hex as well) is that it is prone to leak at the implant-abutment interface (seating surface) due to "lifting" of the abutment under load that may create an intermittent gap resulting in bacteria penetration and subsequent crestal bone loss.

Another alternative interface is an internal/vertical connection implant assembly where the abutment sits "vertically" within the implant assembly and is supported by the internal sidewalls. In addition to this vertically interfacing aspect, many abutments contain a male anti-rotation feature at the bottom and the corresponding implants have a female receptacle (similar to the internal connection implant design). The main benefits of this design are that the two components effectively wedge together, creating a seal impenetrable to bacteria and the abutment receives added lateral support from the implant due to interaction of the abutment sidewalls with the interior surfaces of the implant. However, such designs suffer from vertical location variability. The accuracy of the fit of the final implant restoration (i.e., crown) is largely dependent on the ability to reliably transfer the location of the implant throughout the multiple steps involved in fabricating the restoration. The currently marketed vertical connection implant systems are susceptible to significant vertical location variability, and subsequent customer dissatisfaction. Location variability is undetectable until the very last step in the restorative process when the patient receives their restoration where it becomes apparent the restoration is too high or too low relative to the original tooth. For example, due to the required manufacturing tolerances, each time an abutment (or other male part) is mated with an implant (or other female part) the initial vertical position is destined to change. Further, once the parts are mated and torque is applied to the screw attaching the abutment to the implant, there is relative motion (or vertical displacement) between the male and female components. The magnitude of this motion is dependent on multiple variables, including but not limited to the screw torque, the surface finishes, and the component specifications.

Known vertical implant systems therefore still allow the lateral movement of the abutment in relation to the implant thus causing the possibility of misalignment. It would be desirable to have an abutment implant interface that eliminates vertical location variability. As the vertical connection implant assembly becomes accepted, it is necessary to develop a system that maintains the benefits of this type of design, yet eliminates the known vertical location variability problem. It would also be desirable for a system to create seals between the abutment and implant. The increase in seals in a contemplated system may result in adhesion between the implant and the abutment. Therefore it would be desirable for a removal system to assist in the removal of an abutment that adheres to an implant due to an improved interface.

BRIEF SUMMARY

An example of the present disclosure is a dental restoration system including an implant for attachment to a jaw bone of a patient. The implant includes a cylindrical body having an interior bore formed between a distal end and a proximal end. The implant also includes an abutment interface on the proximal end of the cylindrical body and an anti-rotational cavity formed in the interior bore proximal to the interface. The system also has an abutment including a stem, a post opposite the stem and an interior bore formed through the stem and the post. The abutment also includes an interface section between the post and the stem which interfaces with the abutment interface of the dental implant.

The system includes an abutment removal insert having a cylindrical end insertable into a groove formed in the interior bore of the abutment. An abutment removal tool screw is insertable within the abutment removal insert. The abutment removal tool screw includes a grip and an opposite end. The opposite end causes the abutment removal insert to contact the abutment. The grip is rotatable to cause the opposite end to create force against the implant to cause the abutment to be detached from the implant.

Another example is an abutment removal tool system for removing an abutment from an implant. The abutment includes an interior bore extending therethrough having a groove and an interface in contact with a corresponding interface on the implant. The system includes an abutment removal insert having a cylindrical end insertable into a groove formed in the interior bore of the abutment. The system includes an abutment removal tool screw insertable within the abutment removal insert. The abutment removal tool screw includes a grip end and an opposite end. The opposite end causes the abutment removal insert to contact the abutment. The grip is rotatable to cause the opposite end to create force against the implant to cause the abutment to be detached from the implant.

Another example disclosed is an implant driver tool for imparting rotational force to a dental implant. The dental implant includes an exterior threaded surface and an interior bore having an anti-rotational cavity and a counter bore. The implant driver tool has a shaft having a proximal end and a distal end including a driver section mateable with the anti-rotation cavity of the implant for driving the implant into bone. An end is attached to the driver section for contact with the counter bore to hold the driver tool to the implant. A grip section is coupled to the proximal end of the shaft.

The foregoing and additional aspects and implementations of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 9A is a perspective view of the abutment removal tool screw shown in FIG. 1;

FIG. 9B is a side view of the abutment removal tool screw shown in FIG. 9A;

FIG. 9C is a front view of the abutment removal tool screw shown in FIG. 9A;

FIG. 10A is a perspective view of the abutment removal tool insert shown in FIG. 1;

FIG. 10B is a side view of the abutment removal tool insert shown in FIG. 10A;

FIG. 11A-E are steps of the process of using the abutment removal tool implant and implant driver in FIG. 1 in separating the abutment from the insert;

FIG. 12A is a perspective view of an alternate implant driver tool with a friction fit tapered nose;

FIG. 12B is a close up view of the implant driver tool shown in FIG. 12A showing the fiction fit tapered nose of the tip;

FIG. 12C is a close up view of the implant driver tool shown in FIG. 12A showing the fit taper nose with a bore;

FIG. 12D is a front view of the tip of the taper nose in FIG. 12C;

FIG. 13A is a perspective view of an alternate implant driver tool;

FIG. 13B is a side view of the implant driver tool shown in FIG. 13A;

FIG. 13C is a close up view of the implant driver tool shown in FIG. 13A showing the members of the tip; and FIG. 13D is a front cross-section view of the tip of the implant driver tool shown in FIG. 13A from the perspective of the lines 13D-13D' in FIG. 13C.

Figure 1:
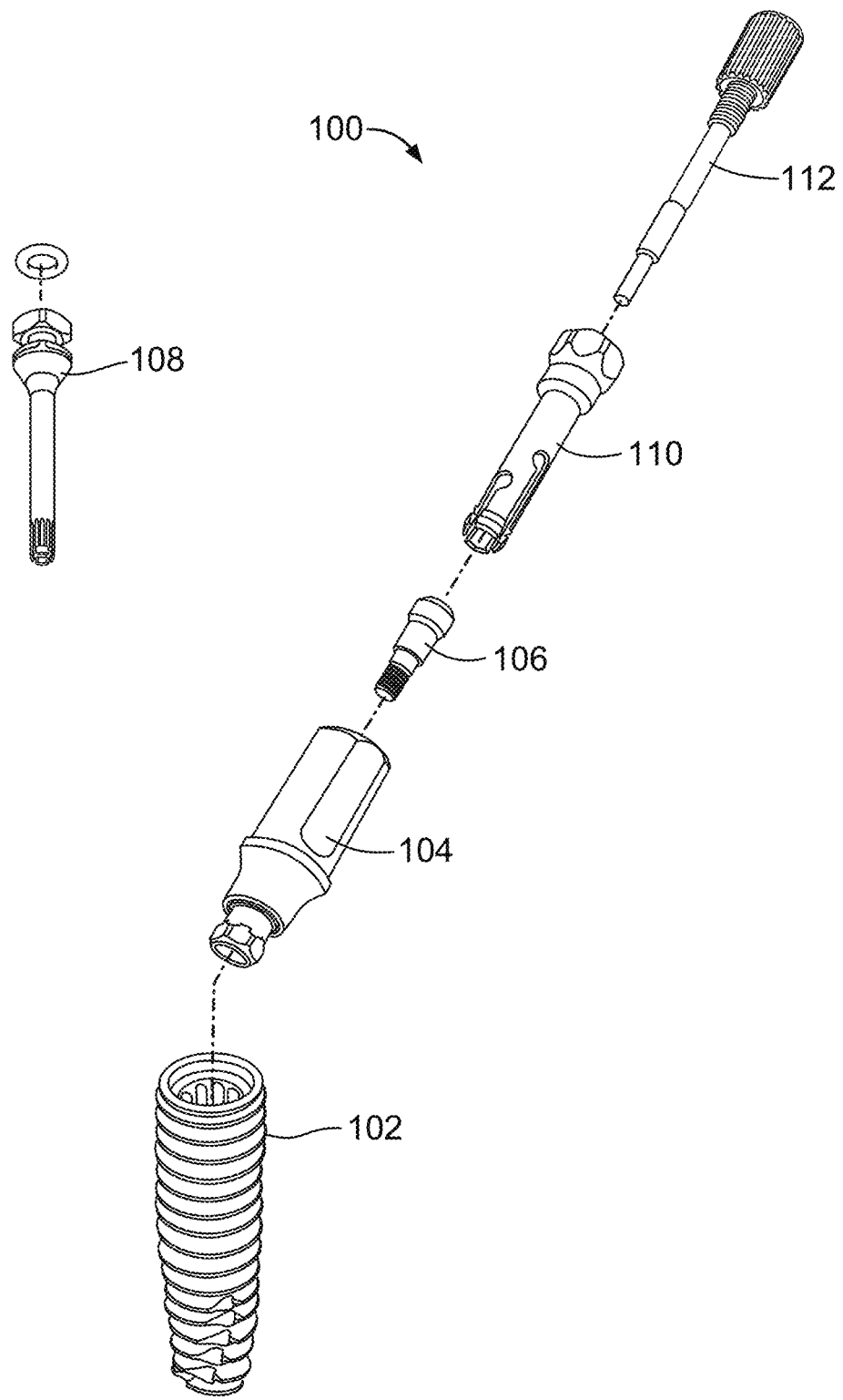
FIG. 1 is an exploded perspective view of an implant and abutment dental restoration system including an implant, an abutment, an insert screw, an implant driver, a removal tool, and a removal tool screw.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

FIG. 1 is an exploded perspective view of the implant and abutment installation system 100 including an implant 102, an abutment 104, an abutment screw 106, and an implant driver tool 108. FIG. 1 also shows a removal system for the abutment 104 including an abutment removal insert tool 110, and an abutment removal tool screw 112. The components shown in FIG. 1 are used in dental restorative processes. As is known, the implant 102 is implanted into the bone of a patient's jaw. The implant driver tool 108 is used to fix the implant 102 into the bone. The abutment 104 may be a standard part or customized to replace the patient's tooth and is attached to the implant 102. The abutment 104 is fixed to the implant 102 via the abutment screw 106, which may be installed via a screw driver tool. In cases where the abutment 104 must be removed from the implant 102 and cannot be readily removed by hand (after the abutment screw 106 is removed), the abutment removal insert tool 110 is used in conjunction with the removal tool screw 112 to remove the abutment 104 without displacing and or rotating the implant 102.

Figure 2A:
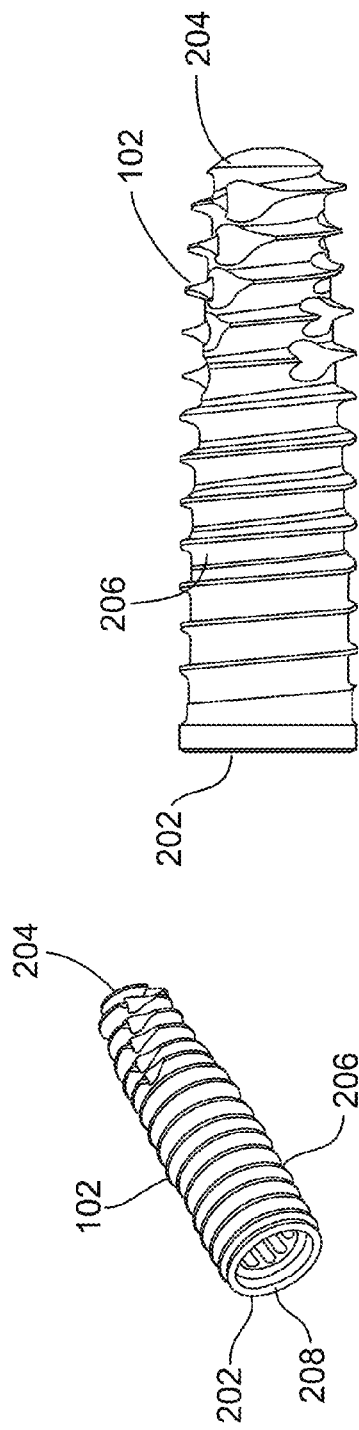
FIG. 2A is a perspective view of the dental implant with a vertical abutment interface shown in FIG. 1.
Figure 2B:
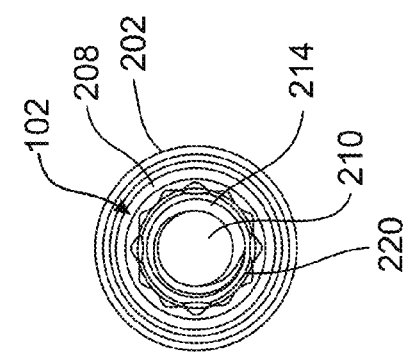
FIG. 2B is a side view of the implant shown in FIG. 2A.
Figure 2D:
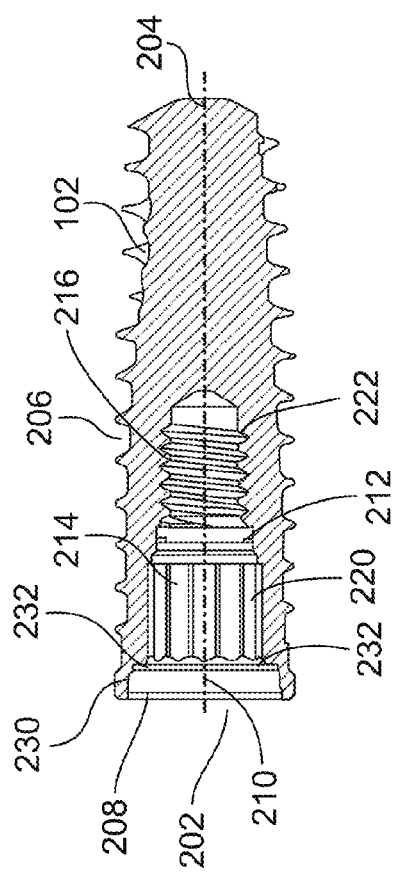
FIG. 2D is a view of the distal end of the implant shown in FIG. 2A.
Figure 2C:
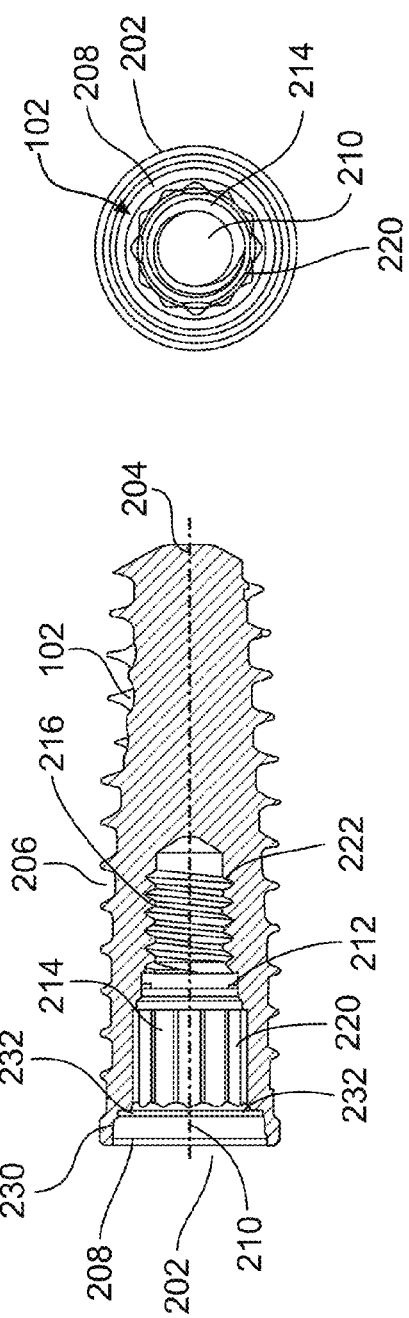
FIG. 2C is a cross-section side view of the implant shown in FIG. 2A.

The implant 102 is further detailed in FIGS. 2A-2D where FIG. 2A is a perspective view of the implant 102, FIG. 2B is a side view of the implant 102, FIG. 2C is a cross-section side view of the implant 102, and FIG. 2D is a view of the distal end of the implant 102. The implant 102 comprises a proximal end 202, a distal end 204 opposite the proximal end 202 and at least one thread 206 disposed therebetween for screwing the implant 102 into the bone of a patient. The proximal end 202 includes an interface 208 adapted to guide the abutment 104 in FIG. 1 when seating the abutment 104 in the implant 102. The implant 102 also includes an interior bore 210 that extends distally from the proximal end 202 toward the distal end 204. The interior bore 210 includes a first anti-rotation cavity 214 and a second anti-rotation cavity 216 distal of the first anti-rotation cavity 214. The interface 208 is concentrically located around the interior bore 210 and is proximal to the first anti-rotation cavity 214. A counter bore 212 is formed between the two cavities 214 and 216.

As shown in detail in FIG. 2C, the two cavities 214 and 216 are separate, distinct and slightly spaced apart, and are connected with a series of concentric steps including the counter bore 212. Other arrangements, however, are equally suitable, such as, for example, where the cavities are adjacent with a tapered transition, or spaced apart and connected by one or more cavities. As will be explained below, the counter bore 212 is fabricated at a narrower diameter than the first cavity 214 to assist in fixing an implant driver tool such as the implant driver tool 108 in FIG. 1 to the implant 102.

Focusing on FIGS. 2C and 2D, the first anti-rotation cavity 214 of implant 102 includes a multi-sided socketed interior surface 220. The socketed interior surface 220 has a plurality of obtuse interior angles in a double hexagonal shape, but other socket shapes may be used. The second anti-rotation cavity 216 includes a threaded interior surface 222 that accepts the abutment screw 106 in FIG. 1.

For some applications, at least one of the anti-rotation cavities 214 and 216 is adapted to mate with a conventional driving tool, for example, a tool with a working end comprising a square, a pentagon, a hexagon, an octagon, etc. Some tools are described in detail such as the implant driver tool 108 shown in detail in FIGS. 8A-8C and the implant driver tool 1200 shown in detail in FIGS. 12A-12B. The cavities 214 or 216 may also be used to hold the abutment 104. However, the other cavity may be adapted to mate with an abutment stem having a predetermined shape other than the cavity that holds the driving tool.

The interface 208 is cylindrically shaped having an interior surface ending in a radially curved annular inner surface 230 proximate the first anti-rotation cavity 214. The annular inner surface 230 transitions to a flat circular vertical stop surface 232 that borders the first cavity 214. As will be explained below, the radially curved inner surface 230 and the vertical stop surface 232 function to guide the abutment 104 and prevent vertical location variability of the abutment 104 relative to the implant 102. The contact of the inner surface 230 and the vertical stop surface 232 of the interface 208 also form seals to prevent gaps in the interface between the implant 102 and the abutment 104.

Figure 3A:
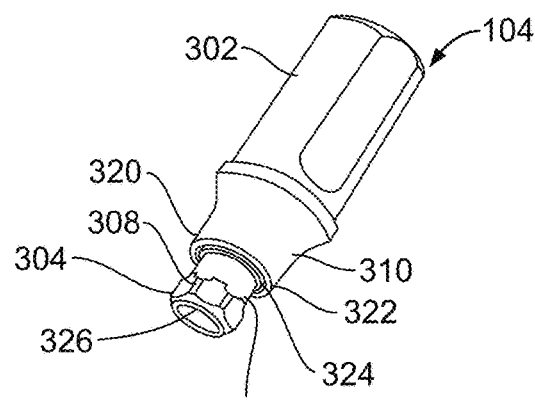
FIG. 3A is a perspective view of the abutment with a vertical implant interface shown in FIG. 1.
Figure 3B:
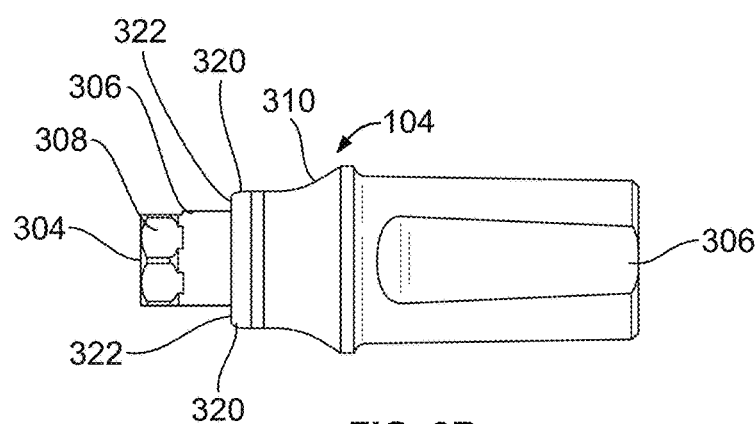
FIG. 3B is a side view of the abutment shown in FIG. 3A.
Figure 3C:
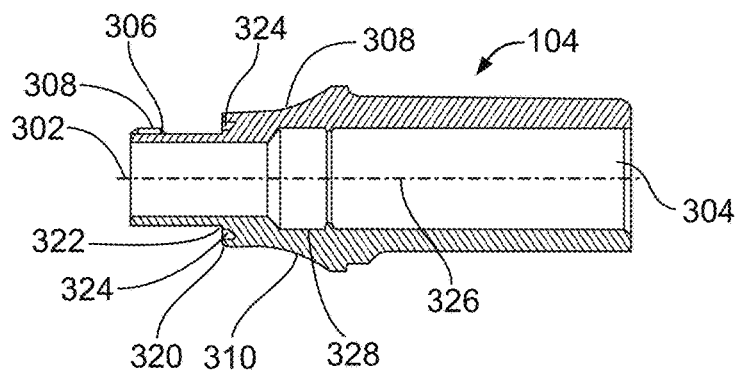
FIG. 3C is a cross-section side view of the abutment shown in FIG. 3A.
Figure 3D:
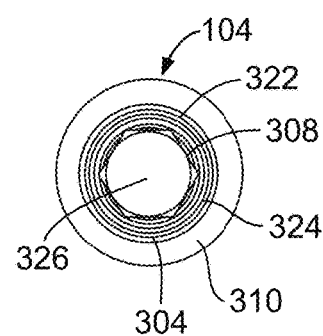
FIG. 3D is a front view of the abutment shown in FIG. 3A.

FIG. 3A-3D are views of the abutment 104 shown in FIG. 1 where FIG. 3A is a perspective view of the abutment 104, FIG. 3B is a side view of the abutment 104, FIG. 3C is a cross-section side view of the abutment 104, and FIG. 3D is a front view of the abutment 104. The abutment 104 comprises a post 302 and a stem 304 extending in a relative downward direction from the post 302. The stem 304 includes a locking portion 306 adapted to be positioned in the first anti-rotation cavity 214 when the abutment 104 is positioned in the implant 102. Accordingly, the locking portion 306 has a multi-sided exterior surface 308 that is adapted to rotationally-lockingly engage the interior multi-sided socketed surface 220 of the first anti-rotation cavity 214 in FIG. 2C, wherein the abutment 104 is prevented from rotating relative to the implant 102.

The abutment 104 includes a transitional section 310 between the post 302 and the stem 304. The transitional section 310 is roughly conical in shape with a larger end connected to the post 302 and an opposite smaller end connected to the stem 304. The smaller end of the transitional section 310 mates with the interface 208 of the implant 102 in FIGS. 2A-2D. The transitional section 310 includes an outer surface that has a curved shape from the larger end with the larger diameter closest to the post 302 to the opposite end with a smaller diameter connected to the stem 304. A radially shaped annular outer surface 320 terminates at the smaller end of the transitional section 310. The outer surface 320 forms a circular vertical stop surface 322 forming the bottom of the transitional section 310 from which the stem 304 protrudes. The circular vertical stop surface 322 includes a circular groove 324 that is cut into the transitional section 310. The circular groove 324 in this example is cut to a depth of approximately 0.012 inches. The circular groove 324 may be cut to a depth of 0.010 to 0.020 inches or deeper or shallower if desired.

In the abutment 104, a through-bore 326 extends through the post 302, the stem 304, and the transitional section 310 to allow the abutment screw 106 shown in FIG. 1 to be inserted therein. The abutment screw 106 is inserted into the through-bore 326 in the abutment 104 to threadably engage the threads of the interior surface 222 of the implant 102 as shown in FIG. 2C. The through-bore 326 also includes a groove 328 that is formed to roughly mate with the abutment removal insert tool 110 as will be explained below.

In FIG. 1, the abutment screw 106 includes a screw head adapted to mate with a driving tool (not shown) with a screw head such as an Allen wrench, a square driver, a flat head screwdriver, a Phillips screwdriver, etc. After the abutment 104 is placed in the implant 102, the abutment screw 106 is inserted in the through-bore 326 of the abutment 104 and the cavity 216 of the implant 102. The driving tool is used to tighten the abutment screw 106 by engaging the threaded interior surface 222 of the cavity 216. After the abutment screw 106 threadably engages the implant 102, the abutment screw 106 acts to retain the abutment 104 in the implant 102.

Figure 4A:
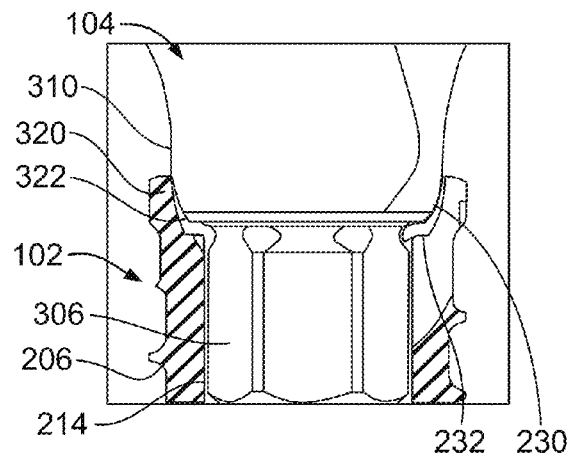
FIG. 4A-B are perspective side cutaway views of the initial contact and final contact between abutment and implant in FIG. 1 when seating the abutment in the implant.
Figure 4B:
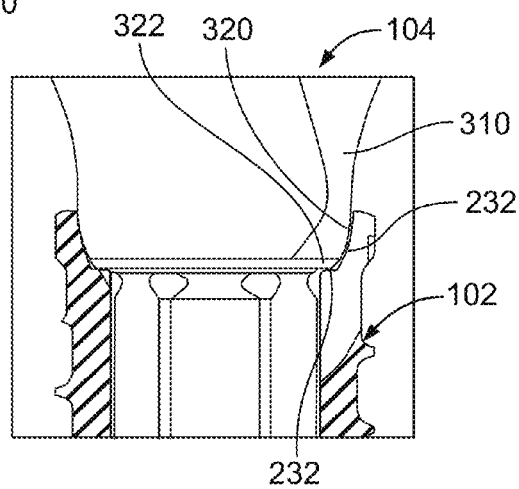
Figures 5A, 5B, 5C:
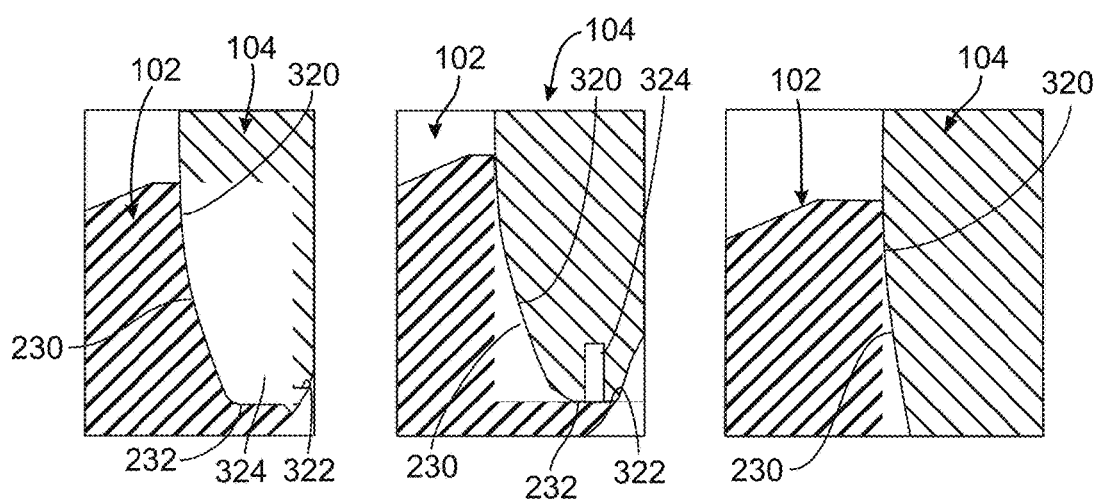
FIG. 5A-C are side cutaway views of the contacts between the abutment and implant in FIG. 1 in the process of seating the abutment in the implant.

The combination of the radially shaped annular outer surface 320 and the vertical stop surface 322 allows for a seal between abutment 104 and the implant 102. The vertical stop surface 322 prevents vertical location variability of the abutment 104 relative to the implant 102. The insertion of the abutment 104 in the implant 102 may be shown with reference to FIGS. 4A-4B and 5A-5C. FIGS. 4A-4B are perspective side cutaway views of the initial contact and final contact between abutment 104 and implant 102 in FIG. 1 while FIG. 5A-C are side cutaway views of the contacts between the abutment 104 and implant 102 in the process of locating the abutment 104 on the implant 102. For convenience of illustration, the groove 324 has been omitted from FIGS. 4A-4B and FIG. 5C. As shown in FIGS. 4A and 5A, the radially shaped outer surface 320 is inserted into the interface 208 of the implant 102 when the stem 304 is inserted in the cavity 214. The radially shaped outer surface 320 initially contacts the radially curved inner surface 230 of the interface 208. The abutment 104 is inserted into the implant 102 until the vertical stop surface 322 contacts the flat vertical stop surface 232 bordering the cavity 214 as shown in FIGS. 4B and 5B.

The radial interface 322 and the vertical stop surface 232 eliminate location variability from abutment 104 being seated in the implant 102. As may be seen in FIGS. 4 and 5, the vertical stop surface 232 of the implant 102 is connected to the radially curved inner surface 230. All the components in the restorative process requiring vertical location control use the vertical stop surface 232 for vertical location, so there is no error accumulated throughout the restorative process using the implant 102 and the abutment 104. During the restorative process involving the fabrication of the abutment 104, there is no contact with the radially curved sidewalls of the surface 320 for certain components because no seal is required. This is achieved in intermediate steps of the restorative process for these components by removing the radial interface on intermediate components such as the impression coping and the implant analog, thus ensuring that the abutment 104 contacts the vertical stop in the final assembly and prevent distortions from sidewall contact when using the intermediate components. Thus, the radially curved inner surface 230 of the implant 102 interfaces with the radially shaped outer surface 320 of the abutment 104, but the vertical position of the finish location is controlled by the radial interface 322 in contact with the vertical stop surface 232. This interface results in a first radial seal on the radially shaped outer surface 320 of the abutment 104 in contact with the radially curved inner surface 230 of the implant 102 as shown in FIG. 5C. A second horizontal seal on the bottom of the transitional section 310 is formed via the contact of the radial interface 322 of the abutment 104 with the vertical stop surface 232 of the implant 102.

Figure 4C:
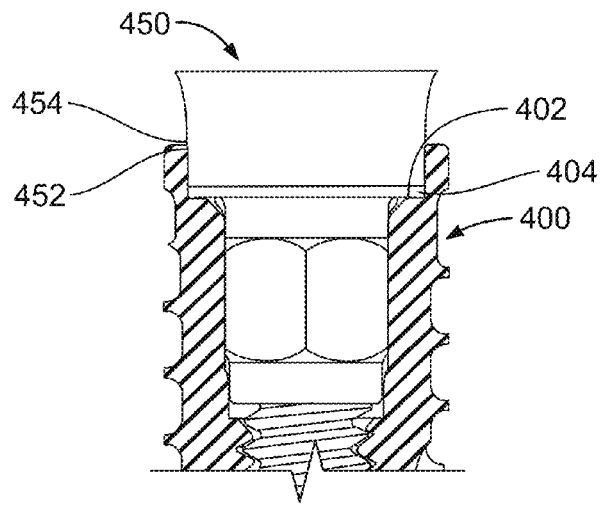
FIG. 4C-4E are side cutaway views of seating an alternate abutment in an alternate implant with a stop member for vertical location.
Figure 4D:
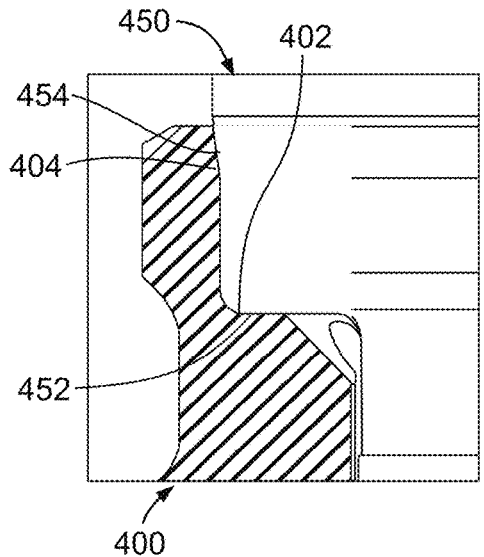
Figure 4E:
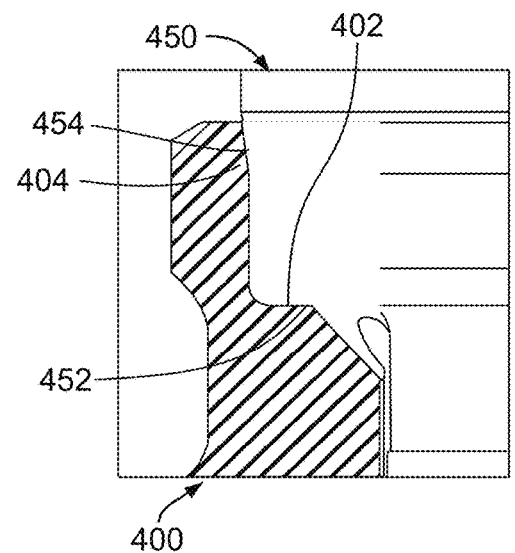

The radial interface 322 and the vertical stop surface 232 shown in FIG. 4A-4B and FIG. 5A-5C may be used with non-curved interfaces. FIG. 4C shows an implant 400 with a standard conical interface having a vertical stop surface 402 contacting an abutment 450. FIG. 4D is a close up view of the interface between the implant 400 and the abutment 450 prior to connection of the components while FIG. 4E is a close up view of the interface between the implant 400 and the abutment 450 when a seal has been established. The abutment 450 has a radial interface 452 that provides contact with the vertical stop surface 402. The vertical stop surface 402 eliminates location variability from the abutment 450 being seated in the implant 400. In this example, the abutment 450 has a standard conical interface surface 454 while the implant has a conical inner surface 404. As may be seen in FIGS. 4C and 4E, the vertical stop surface 402 of the implant 400 is connected to the conical inner surface 404. All the components in the restorative process requiring vertical location control use the vertical stop surface 402 for vertical location, so there is no error accumulated throughout the restorative process using the implant 400 and the abutment 450. During the restorative process involving the fabrication of the abutment 450, there is no contact with the conical surface 454 for certain components because no seal is required. This is achieved in intermediate steps of the restorative process for these components by removing the radial interface on intermediate components such as the impression coping and the implant analog, thus ensuring that the abutment 450 contacts the vertical stop surface 402 of the implant 400 in the final assembly and prevent distortions from sidewall contact when using the intermediate components. Thus, the conical inner surface 402 of the implant 400 interfaces with the conical surface 454 of the abutment 450, but the vertical position of the finish location is controlled by the vertical stop 402. A seal on the bottom of the transitional section of the abutment 450 is formed via the contact of the radial interface 452 of the abutment 450 with the vertical stop surface 402 of the implant 400. In this example, the angle of the conical inner surface 402 of the implant 400 is approximately 16 degrees while the angle of conical surface 454 of the abutment 450 is approximately 20 degrees. The lateral forces are concentrated at the top edge of the implant 400 on the conical inner surface 404 in order to aid in seating the abutment 450 in the implant 400. The contact between the conical inner surface 404 and the conical interface surface 454 also create another seal in addition to the seal between the radial interface 452 against the vertical stop surface 402.

A further benefit of better compliance is realized via the groove 324 on the abutment 104 shown in detail in FIGS. 3A-3D. The groove 324 allows a more compliant interface of the abutment 104 with the implant 102. Due to the groove 324, the interface formed by the radially curved surface 320 of the transitional section 310 has built in flexibility to compress into the groove 324 to allow the radially curved surface 320 to better conform to the radially curved inner surface 230 of the implant 102 and in turn increase the seal contact area between the abutment 104 and the implant 102. This flexibility is achieved by removing material from the cross-section of transitional section 310 of the abutment 104 to form the groove 324. Further, because the abutment 104 is compliant with the implant 102, the design may be manufactured more robustly, as the system will work under a wider range of tolerance configurations.

Figure 6A:
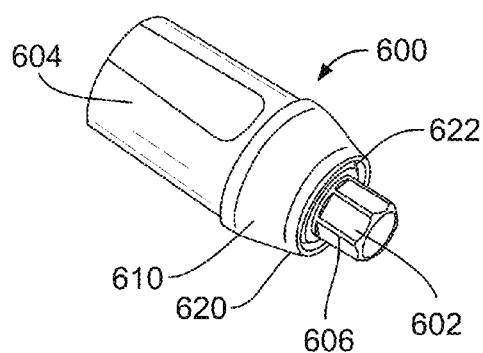
FIG. 6A is a perspective view of an alternate design for the abutment with a groove in the interface to facilitate fit into an implant.
Figure 6B:
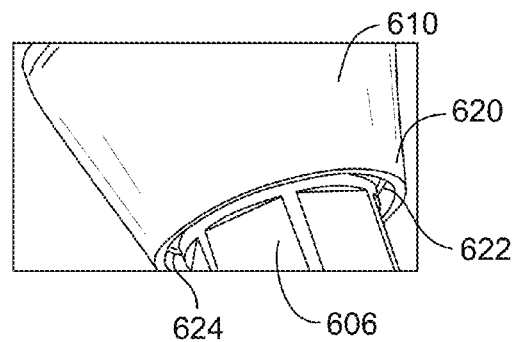
FIG. 6B is a side view of the abutment shown in FIG. 6A.
Figure 6C:
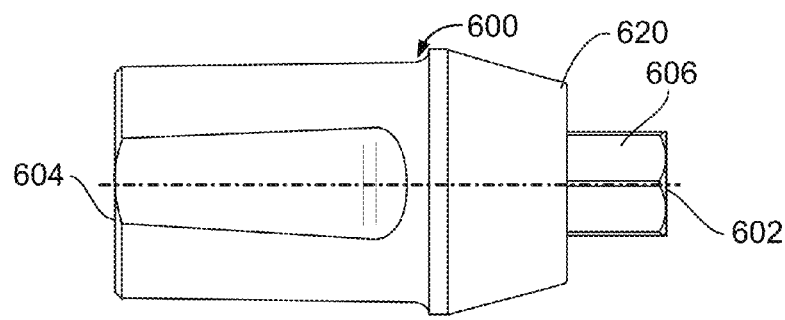
FIG. 6C is a cross-section side view of the abutment shown in FIG. 6A.
Figure 6D:
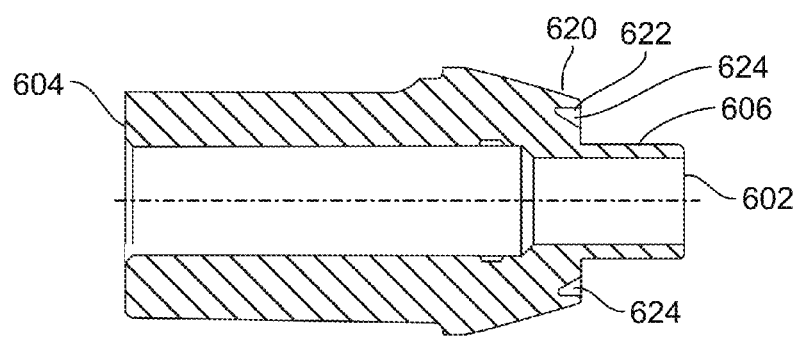
FIG. 6D is a close up perspective view of the groove on the alternate design for the abutment shown in FIG. 6A

The use of a groove such as the groove 324 shown in FIG. 3A-D in the interface of the abutment 104 may be used with conventional interfaces for vertical implant connection of abutments to any implant similar to the implant 102 in FIG. 1. For example, FIGS. 6A-6D are views of an abutment 600 having a conventional conical tapered interface but using the groove feature. FIG. 6A is a perspective view for the abutment 600 with a groove into the interface to the implant, FIG. 6B is a side view of the abutment 600 shown in FIG. 6A, FIG. 6C is a cross-section side view of the abutment 600 shown in FIG. 6A, and FIG. 6D is a close up perspective view of the groove on the alternate design for the abutment 600 shown in FIG. 6A.

The abutment 600 comprises a post 602 and a stem 604 extending in a relative downward direction from the post 602. The stem 604 includes a locking portion 606 adapted to be positioned in the first anti-rotation cavity 214 of the implant 102 when the abutment 104 is positioned in the implant 102. The locking portion 606 has a multi-sided exterior surface 608 that is adapted to rotationally-lockingly engage an interior multi-sided socketed surface such as the surface 220 of the first anti-rotation cavity 214 in FIG. 2C, wherein the abutment 600 is prevented from rotating relative to the implant.

The abutment 600 includes a transitional section 610 between the post 602 and the stem 604. The transitional section 610 mates with an exterior surface of the implant. The transitional section 610 includes an outer surface that generally slopes from a greater diameter closest to the post 602 to a smaller diameter close to the stem 604. A conically shaped outer surface 620 terminates into a circular vertical stop surface 622. The circular vertical stop surface 622 includes a circular groove 624. The circular groove 624 permits built in flexibility to allow the abutment 600 to better conform to the corresponding shaped inner surface of the implant and in turn increase the seal contact area between the abutment 600 and the implant.

Figure 7A:
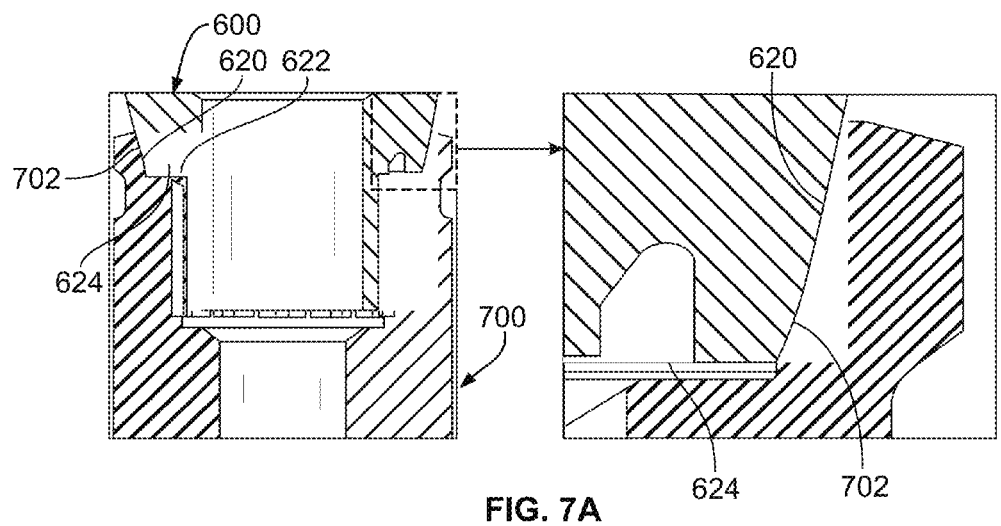
FIG. 7A is a side view of the alternate abutment design in FIG. 6A in contact with an implant.
Figure 7B:
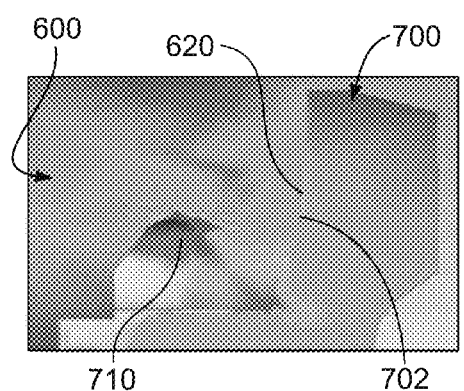
FIG. 7B is a stress diagram of the abutment in FIG. 6A in contact with the implant.

FIG. 7A is a side view of the abutment 600 in FIG. 6A in contact with an implant 700 and FIG. 7B is a stress diagram of the abutment 600 in contact with the implant 700. In this example, the implant 700 is similar to the implant 102, except that the implant 700 has a conventional conical interface surface 702. As may be seen in FIGS. 7A and 7B, a further benefit of better compliance is realized via the groove 624 on the abutment 600 which has a conventional conical interface surface 610. The inset portion of FIG. 7A is an extreme close up of the groove 624 cut into the transitional section 610. The groove 624 allows a more compliant interface of the abutment 600 with the implant 700. Due to the groove 624, the interface formed by the conically shaped outer surface 620 of the transitional section 610 has built in flexibility to compress into the groove 624 to allow the conically shaped outer surface 620 to better conform to the conically sloped interface inner surface 702 of the implant 700 and in turn increase the seal contact area between the abutment 600 and the implant 700. This flexibility is achieved by removing material from the cross-section of transitional section 610 of the abutment 600 to form the groove 624. Further, because the abutment is compliant with the implant 700, the design may be manufactured more robustly, as the system will work under a wider range of tolerance configurations. FIG. 7B shows compressive areas of stress 710 which are compressed from the conical sidewall 702 of the implant 700 pushing into the conically shaped outer surface 620 of the abutment 600.

Figure 8A:
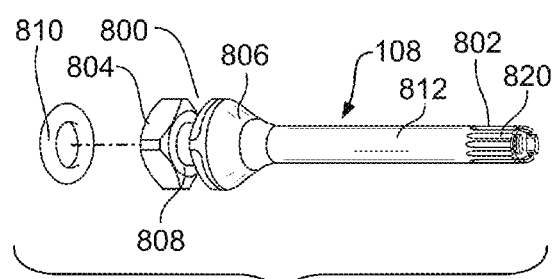
FIG. 8A is a perspective view of the implant driver tool shown in FIG. 1.
Figure 8B:
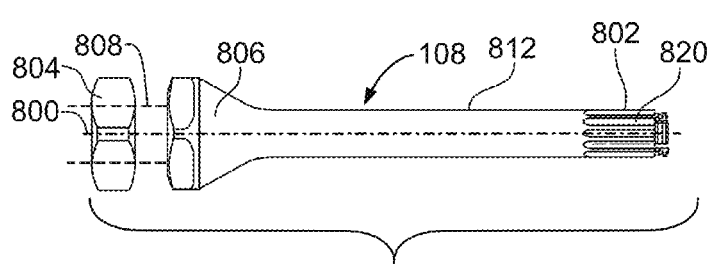
FIG. 8B is a side view of the implant driver tool shown in FIG. 8A.

FIG. 8A is a perspective view of the implant driver tool 108 shown in FIG. 1 and FIG. 8B is a side view of the implant driver tool 108. The implant driver tool 108 is adapted to mate with the first anti-rotation cavity 214 of the implant 102. When the implant driver tool 108 is mated with the implant 102, the driver tool 108 may be rotated to drive the threaded exterior surface 206 of the implant 102 into the bone. The implant driver tool 108 includes a first end 800 and a working end 802 that is adapted to fit within the bore 210 of the implant 102 in FIG. 2C. The first end 800 is a grip section that includes a wrench interface 804 that is spaced from a conical transition section 806 to form an annular groove 808. A resilient ring, such as an O-ring 810, is seated in the annular groove 808 to help retain the implant driver tool 108 in proper engagement with a torque wrench. The implant driver tool 108 has a shaft 812 having a proximal end coupled to the grip section of the first end 800 and a distal end that forms the working end 802. The distal end of the shaft 812 includes a hexagonal male geometry driver section 820 adapted to mate with the socketed interior surface 220 of the anti-rotation cavity 214 of the implant 102. The contact between the driver section 820 and the socketed interior surface 220 of the implant 102 allows the transition of torque force from the driver tool 108 to the implant 102.

Figure 8C:
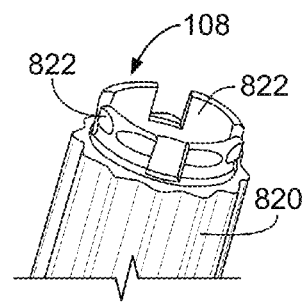
FIG. 8C is a close up view of the implant driver tool shown in FIG. 8A showing the members of the tip.

The wrench interface 804 of the implant driver tool 108 in this example has a four sided exterior surface to interface with a torque wrench that may be used to provide torque to turn the implant driver tool 108 and thereby the implant 102 to engage the threads on the exterior surface 206 with the bone to seat the implant 102. In order to maintain sterile conditions, the implant 102 is generally packed in a sterile package. The driver section 820 includes an end that is inserted in the bore 210 of the implant 102 to allow a user to hold the combined driver tool 108 and attached implant 102. The user may therefore use the implant driver tool 108 to move the implant 102 into the desired location in the bone without contacting the implant 102. FIG. 8C is a close up view of the end of the driver section 820 of the implant driver tool 108 shown in FIG. 8A showing a series of circumferential tips 822 extending from the exterior edge of the driving portion 820 of the working end 802. The diameter of the tips 822 in FIG. 8C are aligned with the counter bore 212 in the implant 102 to provide frictional contact thereby fixing the driver tool 108 to the implant 102.

The seal created by the interface 208 of the implant 102 with the abutment 104 creates the possibility of binding the abutment 104 to the implant 102 once assembled. In certain circumstances, such as replacement due to damage to the restoration, the abutment 104 requires removal from the implant 102. In some cases, the abutment 104 adheres to the implant 102 due to the sealing surfaces of the interface and cannot be removed manually. The abutment removal tool components 110 and 112 may then be used to insure that the abutment 104 may be removed without damaging or displacing the implant 102 if the abutment 104 remains adhered to the implant 102. As will be explained below, the abutment removal tool screw 112 is used in conjunction with the abutment removal insert tool 110 to engage the groove 328 within the through bore 326 of the abutment 104 as shown in FIG. 2C. The abutment removal tool screw 112 forces the abutment removal insert tool 110 into the groove 328 in the bore 326 of the abutment 104. The abutment removal tool insert 110 is prevented from rotating by securing the insert 110 by a wrench that causes the screw 112 to push against the bottom of the inside of the implant 102 when the abutment removal tool screw 112 is turned. The resulting downward force applied by the screw 112 against the implant 102 frees the abutment 104 from the implant 102.

The abutment removal tool screw 112 is shown in FIGS. 9A-9C where FIG. 9A is a perspective view of the abutment removal tool screw 112, FIG. 9B is a side view of the abutment removal tool screw 112, and FIG. 9C is a front view of the abutment removal tool screw 112. The abutment removal tool screw 112 includes a proximal end 902 and a distal end 904. The proximal end 902 includes a grip section 906 that includes a ridged outer surface that allows a grip for turning the abutment removal tool screw 112. The grip section 906 may also be mated with a torque imparting tool such as a wrench to turn the abutment removal tool screw 112. The grip section 906 is connected to a thread section 908 that includes exterior threads 910 that may be engaged with a threaded interior surface of the abutment removal insert tool 110 shown in FIGS. 10A-10E. The thread section 908 is connected to a shaft 912 that extends to the distal end 904.

Figure 10C:
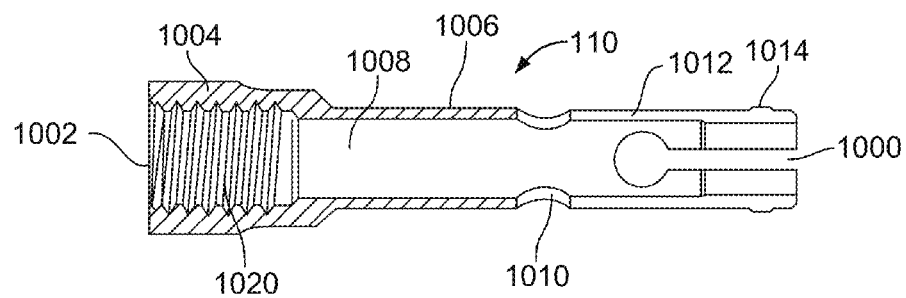
FIG. 10C is a cross-section side view of the abutment removal tool insert shown in FIG. 10A.
Figure 10D:
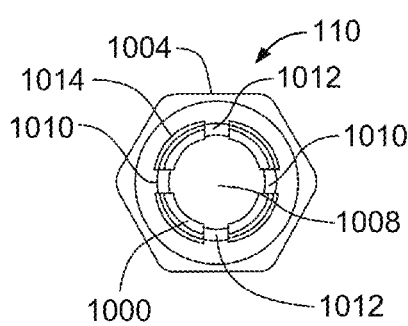
FIG. 10D is a front view of the abutment removal tool insert shown in FIG. 10A.
Figure 10E:
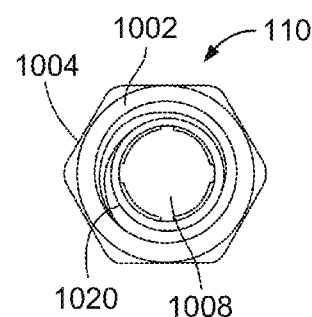
FIG. 10E is a back view of the abutment removal tool insert shown in FIG. 1.

FIGS. 10A-10E show the abutment removal insert tool 110 where FIG. 10A is a perspective view of the abutment removal insert tool 110, FIG. 10B is a side view of the abutment removal insert tool 110, FIG. 10C is a cross-section side view of the abutment removal insert tool 110 along the line 10C-10C' in FIG. 10B, FIG. 10D is a front view of the abutment removal insert tool 110, and FIG. 10E is a back view of the abutment removal insert tool 110. The abutment removal insert tool 110 includes a distal end 1000 and a proximal end 1002. A multi-sided interface 1004 is formed on the distal end 1000 to provide an interface for a wrench. A cylinder 1006 extends from the distal end 1000 to the proximal end 1002. The cylinder 1006 forms an interior bore 1008. Two long notches 1010 are cut from the proximal end 1002 and two short notches 1012 are cut from the proximal end 1002 over part of the length of the cylinder 1006. An annular protrusion 1014 extends out from the cylinder 1006 at the members formed by the notches 1010 and 1012. The end of the interior bore 1008 on the proximal end 1002 includes an interior threaded surface 1020.

Figure 11A:
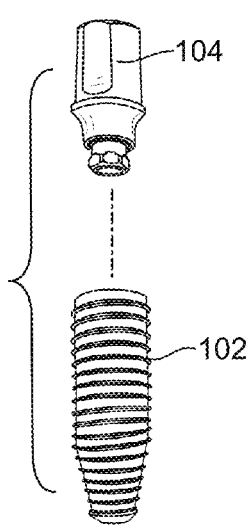
Figure 11B:
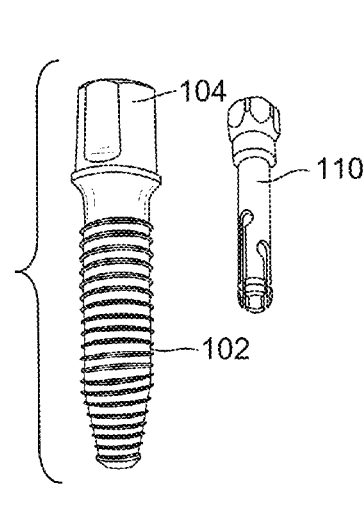

The process of removing the abutment 104 from the implant 102 using the abutment removal tool screw 112 and the abutment removal insert tool 110 is shown in FIGS. 11A-11E. FIG. 11A shows the abutment 104 and the implant 102 prior to connecting the abutment 104 to the implant 102 via the screw 106. FIG. 11B shows the abutment 104 has been assembled to the implant 102 with an abutment screw 106. If it is desired to remove the abutment 104, the abutment screw 106 is removed with a driver tool such as a screwdriver. After the abutment screw 106 is removed, the abutment 104 is stuck to the implant 102 due to excessive side contact and/or interference from the interface described above with reference to FIGS. 4 and 5. As explained above, the abutment removal insert tool 110 in conjunction with the abutment removal tool screw 112 are used to remove the abutment 104 from the implant 102.

Figure 11C:
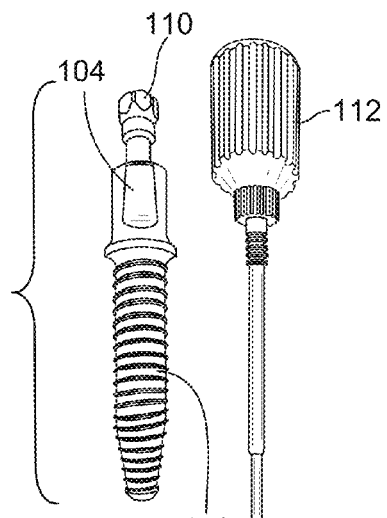

FIG. 11C shows the placement of the abutment removal insert tool 110 in the abutment 104. The protrusions 1014 at the distal end 1000 of the abutment removal insert tool 110 shown in FIG. 10A engage the groove 328 within the through-bore 326 of the abutment 104 shown in FIG. 3C. The abutment removal tool screw 112 is inserted in the interior bore 1008 of the abutment removal insert tool 110 and through the through-bore 326 of the abutment 104. The insertion of the abutment removal tool screw 112 in the interior bore 1008 of the abutment removal insert tool 110 forces the protrusions 1014 against the groove 328 thereby fixing the abutment removal insert tool 110 to the abutment 104.

FIG. 11D shows the resulting placement of the abutment removal tool screw 112 into the abutment removal insert tool 110. The exterior threads 910 of the thread section 908 engage the interior threaded surface 1020 of the abutment removal insert tool 110. The distal end 1000 of the removal tool screw 112 is inserted through the interior bore 1008 of the abutment removal insert tool 110 to the implant 102.

FIG. 11E shows the abutment removal tool 110 held with a wrench 1100 so that it and/or the implant 102 cannot rotate. A user then may grip the grip section 906 of the abutment removal tool screw 112 to turn the abutment removal tool screw 112. The distal end 1000 of the abutment removal tool screw 112 will contact the internal aspect of the implant 102. The resulting contact to the implant 102 will then apply a vertical force to the abutment 104 in relation to the implant 102 as further torque is applied to the abutment removal tool screw 112 translated through the thread section 908 to the interior threaded surface 1020 of the abutment removal insert tool 110. The abutment removal tool screw 112 is turned until the abutment 104 is freed from the implant 102.

Alternate designs may be made for each of the components shown in FIG. 1. For example, a different shaped driver tool may be used for the driver tool 108 such as the driver tool 1200 shown in FIGS. 12A and 12B, where FIG. 12A is a perspective view of the implant driver tool 1200 and FIG. 12B is a close up view of the implant driver tool 1200 shown in FIG. 12A. The implant driver tool 108 includes a first end 1202 and a working end 1204 that is adapted to fit within the bore 210 of the implant 102. The first end 1202 includes a wrench interface 1206 that is spaced from a shaft 1208 to form an annular groove 1210. A resilient ring, such as an O-ring (not shown) is seated in the annular groove 1210 to help retain the implant driver tool 1200 in proper engagement with a torque wrench. The working end 1204 of the implant driver tool 1200 has a hexagonal male geometry driving portion 1220 adapted to mate with the socketed interior surface 220 of the anti-rotation cavity 214 of the implant 102.

FIG. 12B is a close up view of the implant driver tool 1200 shown in FIG. 12A showing a friction fit tapered nose 1222 that replaces the tips 822 shown in FIG. 8C. The tapered nose 1222 fits within the counter bore 212 of the implant 102 and serves to hold the implant driver tool 1200 to the implant 102 to allow a user to manipulate the implant 102 while maintaining sterility of the implant 102. The advantage of the shape of the tapered nose 1222 is ease of manufacture of the implant driver tool 108.

The implant driver tool 1200 shown in FIGS. 12A-12B may have alternative features of the tip to engage the implant to provide torque to the implant 102. An alternative tapered nose section 1250 is shown FIG. 12C which is a close up view of the tapered nose 1250 of the implant driver tool shown in FIG. 12A and FIG. 12D is a front view of the tip of the alternate tip configuration in FIG. 12C. Like elements are labeled with like element numbers in FIGS. 12C and 12D. The working end 1204 of the implant driver tool has a hexagonal male geometry driving portion 1220 adapted to mate with the socketed interior surface 220 of the anti-rotation cavity 214 of the implant 102. The alternative tapered nose 1250 has a circular bore 1252 as shown in FIG. 12D. The circular bore 1252 provides a reduction of the cross-sectional moment of inertia and reduces the stiffness of the tapered nose 1250 to decrease excessive contact between the tip and the implant 102.

FIG. 13A is a perspective view of an alternative implant driver tool 1300 that may be used instead of the implant driver tool 108 shown in FIG. 1. FIG. 13B is a side view of the implant driver tool 1300. The implant driver tool 1300 is adapted to mate with an anti-rotation cavity in an implant. When the implant driver tool 1300 is mated with the implant, the driver tool 1300 may be rotated to drive a threaded exterior surface of the implant into the bone. The implant driver tool 1300 includes a first end 1310 and a working end 1312 that is adapted to fit within the bore of an implant. The first end 1310 is a grip section that includes a wrench interface 1314 that is spaced from a conical transition section 1316 to form an annular groove 1318. A resilient ring, such as an O-ring 1320, is seated in the annular groove 1318 to help retain the implant driver tool 1300 in proper engagement with a torque wrench. The implant driver tool 1300 has a shaft 1322 having a proximal end coupled to the grip section of the first end 1310 and a distal end that forms the working end 1312. The distal end of the shaft 1322 includes a hexagonal male geometry driver section 1330 adapted to mate with a socketed interior surface of the anti-rotation cavity of the implant. The contact between the driver section 1330 and the socketed interior surface of the implant allows the transition of torque force from the driver tool 1300 to the implant.

The wrench interface 1314 of the implant driver tool 1300 in this example has a four sided exterior surface to interface with a torque wrench that may be used to provide torque to turn the implant driver tool 1300 and thereby the implant to engage the threads on the exterior surface with the bone to seat the implant. In order to maintain sterile conditions, the implant is generally packed in a sterile package. The driver section 1330 includes an end that is inserted in the bore of the implant to allow a user to hold the combined driver tool 1300 and attached implant. The user may therefore use the implant driver tool 1300 to move the implant into the desired location in the bone without contacting the implant.

FIG. 13C is a close up view of the end of the driver section 1330 of the implant driver tool 1300 shown in FIG. 13B. FIG. 13D is a close up front view of the driver section 1330 along the line 13D-13D' in FIG. 13C. The driver section 1330 has six tabs 1332 that extend out from the body of the driver section 1330. The six tabs 1332 are formed between sidewalls 1334 that contact similar surfaces in the socketed interior surface of the implant to connect the driver 1300 with the implant. The tabs 1332 are inserted in slots that are formed on the socket interior surface that provide additional contact between the driver 1300 and the implant. The driver section 1330 therefore has six points of contact in the form of the sidewalls 1334 as well as additional contacts from the six tabs 1332 contacting corresponding slots in the socket portion of the implant.

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the invention as defined in the appended claims.

What is claimed is:

1. A dental restoration system comprising:
    an implant for attachment to a jaw bone of a patient, the implant including:
        a cylindrical body having an interior bore formed between a distal end and a proximal end;
        an abutment interface on the proximal end of the cylindrical body;
        an anti-rotational cavity formed in the interior bore proximal to the interface; and
    an abutment including:
        a stem;
        a post opposite the stem;
        an interior bore formed through the stem and the post, the interior bore defining a groove; and
        an interface section between the post and the stem, the interface section interfacing with the abutment interface of the dental implant;
    an abutment removal insert having a cylindrical end insertable into the groove formed in the interior bore of the abutment, the cylindrical end defining an interior bore and including at least two notches extending from an exterior surface of the abutment removal insert to the interior bore of the abutment removal insert forming at least two flexible members, the at least two flexible members including an annular protrusion extending from a surface of the at least two flexible members; and
    an abutment removal tool screw insertable within the abutment removal insert, the abutment removal tool screw including a grip and an opposite end, the opposite end causing the annular protrusion of the abutment removal insert to move into and contact the groove thereby fixing the abutment removal insert tool to the abutment, the grip being rotatable to cause the opposite end to create force against the implant to cause the abutment to be detached from the implant.

2. The dental restoration system of claim 1, further comprising an implant driver tool having a driver section mateable with the anti-rotation cavity of the implant for driving the implant into bone.

3. The dental restoration system of claim 2, wherein the interior bore of the implant includes a counter bore, and the implant driver tool includes an end extending from the driver section for contact with the counter bore to hold the implant to the driver tool.

4. The dental restoration system of claim 3, wherein the end is a tapered nose.

5. The dental restoration system of claim 3, wherein the end includes a plurality of circumferential tips.

6. An abutment removal tool system for removing an abutment from an implant, the abutment including an interior bore extending therethrough having a groove and an interface in contact with a corresponding interface on the implant, the system comprising:
    an abutment removal insert having a cylindrical end insertable into a groove formed in the interior bore of the abutment, the cylindrical end defining an interior bore and including at least two notches extending from an exterior surface of the abutment removal insert to the interior bore of the abutment removal insert forming at least two flexible members, the at least two flexible members including an annular protrusion extending from a surface of the at least two flexible members; and
    an abutment removal tool screw insertable within the abutment removal insert, the abutment removal tool screw including a grip end and an opposite end, the opposite end causing the annular protrusion of the abutment removal insert to move into and contact the groove thereby fixing the abutment removal insert tool to the abutment, the grip being rotatable to cause the opposite end to create force against the implant to cause the abutment to be detached from the implant.

7. The dental restoration system of claim 1, wherein a first notch of the at least two notches has a first length and a second notch of the at least two notches has a second length, the first length being greater than the second notch.

8. The dental restoration system of claim 7, further including:
    a third notch having a third length; and
    a fourth notch having a fourth length, wherein the third length is substantially equal to the first length and the fourth length is substantially equal to the second length, and wherein the third notch is positioned between the second and fourth notch.

9. The abutment removal tool system of claim 6, wherein the abutment removal insert includes an interior threaded surface, and wherein the abutment removal tool screw includes a threaded exterior surface on the opposite end that engages the interior threaded surface of the abutment removal insert.

10. The abutment removal tool system of claim 6, wherein the grip of the abutment removal tool screw is mateable with a wrench to impart rotational force on the abutment removal tool screw.

\* \* \* \* \*